(12) United States Patent
Blivet et al.

(10) Patent No.: US 11,524,170 B2
(45) Date of Patent: Dec. 13, 2022

(54) TRANSCUTANEOUS IRRADIATION DEVICE AND APPLICATION TO THE TREATMENT OF NEURODEGENERATIVE DISEASES

(71) Applicant: REGENLIFE, Montpellier (FR)

(72) Inventors: Guillaume Blivet, Montpellier (FR); Guillaume Moreau, Baillargues (FR)

(73) Assignee: REGENLIFE

( * ) Notice: Subject to any disclaimer, the term of this patent is extended or adjusted under 35 U.S.C. 154(b) by 425 days.

(21) Appl. No.: 16/604,825

(22) PCT Filed: Apr. 13, 2018

(86) PCT No.: PCT/EP2018/059596
§ 371 (c)(1),
(2) Date: Oct. 11, 2019

(87) PCT Pub. No.: WO2018/189393
PCT Pub. Date: Oct. 18, 2018

(65) Prior Publication Data
US 2021/0113846 A1    Apr. 22, 2021

(30) Foreign Application Priority Data

Apr. 14, 2017    (EP) .................................... 17305450

(51) Int. Cl.
*A61N 2/00*    (2006.01)
*A61N 2/02*    (2006.01)
(Continued)

(52) U.S. Cl.
CPC ............. *A61N 2/002* (2013.01); *A61N 2/006* (2013.01); *A61N 2/02* (2013.01); *A61N 2/06* (2013.01);
(Continued)

(58) Field of Classification Search
CPC .... A61N 2005/0645; A61N 2005/0647; A61N 2005/0651; A61N 2005/0659;
(Continued)

(56) References Cited

U.S. PATENT DOCUMENTS

2005/0024853 A1    2/2005  Thomas-Benedict
2007/0129776 A1    6/2007  Robins et al.
(Continued)

FOREIGN PATENT DOCUMENTS

EP            1074275 A1    2/2001

OTHER PUBLICATIONS

Antczak et al., Repetitive transcranial magnetic stimulation for the treatment of cognitive impairment in frontotemporal dementia: an open-label pilot study, Neuropsychiatric Disease and Treatment, Mar. 2018, pp. 749-755, vol. 14.
(Continued)

*Primary Examiner* — Christine H Matthews
(74) *Attorney, Agent, or Firm* — Lerner, David, Littenberg, Krumholz & Mentlik, LLP

(57) ABSTRACT

The technology disclosed herein relates to a transcutaneous irradiation device having a top portion and a bottom portion. The top portion may include one or more transcutaneous irradiation modules configured to be arranged on a head of a user, the top transcutaneous irradiation modules including a top pulsed laser source. The bottom portion may include one or more transcutaneous irradiation modules configured to be arranged on an abdomen of the user, the top transcutaneous irradiation modules including a bottom pulsed laser source. A modulation frequency may be applied to the top and bottom irradiation modules such that the top and bottom pulse laser sources are subjected to a double pulse.

20 Claims, 22 Drawing Sheets

(51) Int. Cl.
*A61N 2/06* (2006.01)
*A61N 5/06* (2006.01)
*A61N 5/067* (2006.01)

(52) U.S. Cl.
CPC .......... *A61N 5/0622* (2013.01); *A61N 5/067* (2021.08); *A61N 2005/066* (2013.01); *A61N 2005/0626* (2013.01); *A61N 2005/0647* (2013.01); *A61N 2005/0651* (2013.01); *A61N 2005/0663* (2013.01)

(58) Field of Classification Search
CPC ...... A61N 2005/066; A61N 2005/0662; A61N 2005/0663; A61N 2/002; A61N 2/006; A61N 2/02; A61N 2/06; A61N 5/0622; A61N 5/067
See application file for complete search history.

(56) References Cited

U.S. PATENT DOCUMENTS

| | | | |
|---|---|---|---|
| 2009/0030489 | A1 | 1/2009 | Asvadi et al. |
| 2010/0204762 | A1 | 8/2010 | De Taboada et al. |

OTHER PUBLICATIONS

Haley et al., Pharmacological Effects Produced By Intracerebral Injection Of Drugs In The Conscious Mouse, Brit. J. Pharmacol., Mar. 1957, pp. 12-15, vol. 12.
Hermes-Lima et al., Quantification of Lipid Peroxidation in Tissue Extracts Based on Fe(III)Xylenol Orange Complex Formation, Free Radical Biology & Medicine, Sep. 1995, pp. 271-280, vol. 19, No. 3.
Hiramatsu et al. , Effects of nocistatin on nociceptin-induced impairment of learning and memory in mice, European Journal of Pharmacology, Feb. 1999, pp. 151-155, vol. 367.
International Search Report for Application No. PCT/EP2018/059596, dated Jun. 8, 2018, pp. 1-4.
Itoh et al., Dynorphin A-( 1-13) markedly improves scopolamine-induced impairment of spontaneous alternation performance in mice, European Journal of Pharmacology, Jun. 1993, pp. 31-345, vol. 236.
Koch et al., Transcranial magnetic stimulation of the precuneus enhances memory and neural activity in prodromal Alzheimer's disease, NeuroImage, available online Dec. 2017, pp. 302-311, vol. 169.
Maurice et al., Reversion of b25-35-amyloid peptide-induced amnesia by NMDA receptor-associated glycine site agonists, Brain Research, Aug. 1996, pp. 249-253, vol. 731.
Maurice et al., Sigma1 (s1) Receptor Agonists And Neurosteroids Attenuate B25-35-Amyloid Peptide-Induced Amnesia In Mice Through A Common Mechanism,, Neuroscience, Mar. 1998, pp. 413-428, vol. 83, No. 2, Elsevier Science Ltd.
Meunier et al., The anti-amnesic and neuroprotective effects of donepezil against amyloid b25-35 peptide-induced toxicity in mice involve an interaction with the s1 receptor, British Journal of Pharmacology, published online Oct. 2006, pp. 998-1012, vol. 149.
Meunier et al., The y-secretase inhibitor 2-[(1R)-1-[ (4-chlorophenyl)sulfonyl] (2,5-difluorophenyl) amino]ethyl-5-fluorobenzenebutanoic acid (BMS-299897) alleviates Ab1-42 seeding and short-term memory deficits in the Ab25-35 mouse model of Alzheimer's disease, European Journal of Pharmacology, available online Nov. 2, 2012, pp. 193-199, vol. 698.
Parashar et al., Gut microbiota: Implications in Parkinson's disease, Parkinsonism and Related Disorders, May 2017, pp. 1-7, vol. 38.
Pridmore & Pridmore, Repetitive transcranial magnetic stimulation in the treatment of depression, AJGP, Mar. 2018, pp. 122-125, vol. 47, No. 3.
Villard et al., Anti-amnesic and neuroprotective potentials of the mixed muscarinic receptorfsigmat (s1) Ligand ANAVEX2-73, a novel aminotetrahydrofuran derivative, Journal of Psychopharmacology, Aug. 2011, pp. 1101-1117, vol. 25, No. 8.
Villard et al., Antiamnesic and Neuroprotective Effects of the Aminotetrahydrofuran Derivative ANAVEX 1-41 Against Amyloid b25_35-Induced Toxicity in Mice, Neuropsychopharmacology, published online Dec. 2008, pp. 1552-1566, vol. 34.

TRANSCUTANEOUS IRRADIATION DEVICE AND APPLICATION TO THE TREATMENT OF NEURODEGENERATIVE DISEASES

CROSS-REFERENCE TO RELATED APPLICATIONS

The present application is a national phase entry under 35 U.S.C § 371 of International Application No. PCT/EP2018/059596 filed Apr. 13, 2018, which claims priority from European Patent Application No. 17305450.3 filed Apr. 14, 2017, all of which are hereby incorporated herein by reference.

FIELD OF THE INVENTION

The invention falls within the field of treatment by transcutaneous irradiation.

The invention relates more particularly to a device allowing the implementation of a treatment by transcutaneous irradiation.

The scope of the device of the invention falls within the field of the treatment of neurological diseases.

PRIOR ART

Transcutaneous irradiation is a known technique by which radiation of waves or particles is emitted in contact with the skin and penetrates deeply.

These techniques include photobiomodulation and low-level laser therapy (LLLT) using light-emitting diodes (LEDs) and laser diodes, respectively, to repair and regenerate damaged tissues. This technique consists of positioning a probe on a patient's skin and performing photonic emission for a given time in the damaged tissue area. The probe, for example, marketed by THOR, includes an emission head placed on the skin, a handle to hold the emission head and power cables connected to a control unit. The emission head is held in place by the practitioner throughout the session.

These transcutaneous irradiation techniques, particularly by phototherapy, also apply to neurological and/or psychiatric treatments. This is called transcranial irradiation. In this case, a visible-to-infrared light emission probe, of the type described above, is positioned and held on the surface of the patient's head by the practitioner. This technique can be used to treat neurological disorders therapeutically to restore neurological faculties, stop the progression of cognitive disorders, such as neurodegenerative diseases such as Alzheimer's, or maintain a quality of life.

Moreover, the application of these techniques to neurological treatments requires a precise positioning of the irradiation source directed towards a part of the brain involved in the disorder to be treated. It is of course a matter of targeting only the area concerned, at the risk of affecting a neighbouring area. To do this, a device known and marketed by NEUROTHERA provides a probe support forming a helmet and comprising rings distributed over the patient's head. The helmet is held in position by means of a strap with a chin strap that attaches to two peripheral rings on each side. Each ring is an indicator of position towards a target area of the brain. The probe is positioned by the practitioner at a ring and held in this position for the duration of the treatment.

Finally, another technique used in the treatment of neurological or psychiatric disorders is transcranial magnetic stimulation. This technique consists of applying one or a series of magnetic pulses to the cerebral cortex. Effects have been observed in the treatment of Alzheimer's disease (Koch et al., 2018. *Neuroimage.* 169:302-311), some frontotemporal lobar degeneration (Antczak et al., 2018. *Neuropsychiatr Dis Treat.* 14:749-755) and depression (Pridmore & Pridmore, 2018. *Aust J Gen Pract.* 47(3):122-125).

Here, the Inventors have developed a multi-targeted and multimodal approach, combining photobiomodulation, low-level laser therapy and magnetic stimulation. Surprisingly, the combination of treated anatomical targets and these techniques offers a synergistic effect in the treatment of neurodegenerative diseases, such as Alzheimer's, Parkinson's or Huntington's.

DISADVANTAGES OF THE PRIOR ART

Irradiation techniques as described above do not provide sufficiently satisfactory results on the evolution of neurological disorders.

In addition, the device marketed by NEUROTHERA is insufficient to ensure precise positioning of the light emission towards a target area. Indeed, the holding of the probe by the practitioner can cause a change in the angle of the light emission even when the probe remains in position in the ring. In addition, the practitioner must necessarily hold the probe during treatment. Moreover, it is not possible, in this system, to perform simultaneous treatments of several areas of the brain given that each probe is held in place by the practitioner and that a cumbersome control device is connected to the probe. However, the efficacy of some neurological treatments may depend on the possibility of irradiating several areas at the same time to simultaneously stimulate targeted parts of the brain.

OBJECTIVES OF THE INVENTION

The invention is primarily aimed at a transcutaneous irradiation device with substantial efficacy on the symptoms of neurological and/or psychiatric diseases such as Alzheimer's disease.

The invention also includes a device for performing transcutaneous irradiation on specific areas of the body. In particular, the invention aims at a system ensuring a positioning adapted to the morphology of the patient's head and abdomen of the radiation source(s).

DISCLOSURE OF THE INVENTION

To this end, the transcutaneous irradiation device of the invention is essentially characterised in that it comprises a top portion (1) suitable for being positioned on the head (3) of a user and comprising at least one transcutaneous irradiation module (10) consisting of at least one irradiation source (14a, 14b, 14c); and a bottom portion (9) suitable for being positioned on the abdomen (16) of the user and comprising at least one transcutaneous irradiation module (10) consisting of at least one irradiation source (14a, 14b, 14c).

The device of the invention may also include the following optional features considered individually or in all possible technical combinations:
  each transcutaneous irradiation module (10) comprises at least one pulsed laser source (14a);
  the pulsed laser source (14a) generates a beam emitting in the infrared spectrum, said beam having a wavelength between 700 and 1200 nanometres and a pulse train comprising:

a pulse duration between 20 and 200 nanoseconds;
a pulse train repetition frequency between 1 and 25 kHz included;
an impulse power of between 0.5 and 12 watts inclusive; and
a voltage between 2 and 5 volts inclusive;
the beam has a wavelength between 800 and 900 nanometres, preferably about 850 nanometres;
the pulse duration of the beam generated by the laser source (14a) is between 75 and 150 nanoseconds, preferably between 90 and 110 nanoseconds;
the repetition frequency of the beam generated by the laser source (14a) is between 10 and 15 kHz inclusive, preferably about 15 kHz;
the impulse power of the beam generated by the laser source (14a) is between 1 and 7 watts inclusive;
each transcutaneous irradiation module (10) comprises at least one light-emitting diode (14b, 14c) generating a beam emitting in the visible spectrum or in the infrared spectrum;
each transcutaneous irradiation module (10) comprises at least:
 a pulsed laser source (14a) generating a beam emitting in the infrared spectrum;
 a light-emitting diode or a laser source generating a beam emitting in the red spectrum (14b), and;
 a light-emitting diode generating a beam emitting in the infrared spectrum (14c);
the beam emitting in the red spectrum generated by the at least one light-emitting diode or laser source (14b) has a wavelength between 600 and 700 nanometres, and in that the beam emitting in the infrared spectrum generated by the at least one light-emitting diode (14c) has a wavelength between 700 and 1200 nanometres;
the beam emitting in the red spectrum generated by the at least one light-emitting diode or laser source (14b) has a wavelength of 620 and 650 nanometres, preferably about 640 nanometres or about 625 nm;
the beam emitting in the infrared spectrum generated by the at least one light-emitting diode (14c) has a wavelength of about 850 nanometres;
each transcutaneous irradiation module (10) further comprises a source generating a static magnetic field (18), preferably a magnet or an electromagnet;
the source generating a static magnetic field (18) comprises a ring shape intended to be arranged perpendicular to the plane of which the transcutaneous irradiation is generated by the at least one irradiation source (14a, 14b, 14c);
the device includes means for applying the irradiation by the at least one irradiation source (14a, 14b, 14c) at frequencies below 1000 hertz (inclusive), preferably between 1 and 1000 hertz (inclusive);
the irradiation application means comprises a module for synchronising the emissions of the transcutaneous irradiation module of the top portion (1) with the emissions of the transcutaneous irradiation module of the bottom portion (9), said beams being transmitted at an overall modulation frequency:
 of about 9 to 11 Hz, preferably about 10 Hz for each of the transcutaneous irradiation modules (10) of the top (1) and bottom (9) portion; or
 of about 9 to 11 Hz, preferably about 10 Hz for each of the transcutaneous irradiation modules (10) of the top portion (1) and about 900 to 1000 kHz, preferably about 1000 Hz for each of the transcutaneous irradiation modules (10) of the bottom portion (9);

the device comprises at least two transcutaneous irradiation modules (10) symmetrically arranged on the user's head, and at least two transcutaneous irradiation modules (10) arranged on the user's abdomen, preferably symmetrically arranged;
at least one irradiation source (14a, 14b, 14c) is held within a holding means of substantially cylindrical shape, said holding means being intended to be in contact with a patient so that the beam is emitted parallel to the axis of the cylinder;
the device comprises at least two irradiation modules symmetrically arranged on the user's head, and at least two irradiation modules arranged on the user's abdomen, preferably symmetrically arranged;
each module is fixed to a module support which includes means for positioning said support at the level of the area to be irradiated, and at least one ring made of an elastic and/or flexible material and suitable for fixing said irradiation module by elastic grip;
the module support comprises a plurality of rings connected together by connecting elements forming a transcranial irradiation module support suitable for being positioned on a user's head;
the rings are symmetrically arranged on either side of an axis coinciding with the centre axis of the head when the support is in place on the user's head, the rings include peripheral rings, at least some of which are not connected to each other by connecting elements;
the peripheral rings are not connected to each other by connecting elements;
the rings comprise second peripheral rings and four central rings, at least some second peripheral rings are not connected to each other by connecting elements, and the four central rings are connected to each other by connecting elements;
the support includes a controlled tightening strap comprising at least one connecting part connecting the peripheral rings;
the strap comprises a chin strap extending on each side of the support to two connecting elements which are intended to be respectively arranged on each side of a user's ear and which form a junction between said chin strap and said connecting part;
the inner face of each ring includes a groove to help fix the dedicated module;
the rings are made of a flexible and/or elastic material;
the device of the invention comprises a support as described above, and the irradiation module(s) are adapted to be coaxially fixed on the ring of the support.

The invention also relates to a system comprising the device of the invention and a control console comprising a control interface for configuring the parameters of each of the at least one irradiation source (14a, 14b, 14c) and a communication interface for providing digital control instructions to the said device.

The invention also relates to the device or system according to the present invention, configured for the prevention or treatment of neurological disorders and/or neurodegenerative diseases, preferably for the prevention or treatment of Alzheimer's disease, Parkinson's disease and/or Huntington's disease.

The invention also relates to the application of the device as described above for the treatment of neurological disorders and/or the treatment of neurodegenerative diseases, such as Alzheimer's disease, Parkinson's disease or Huntington's disease.

PRESENTATION OF THE FIGURES

Other features and advantages of the invention will emerge clearly from the description given below, for information purposes only and without limitation, with reference to the appended figures.

Figure 11:
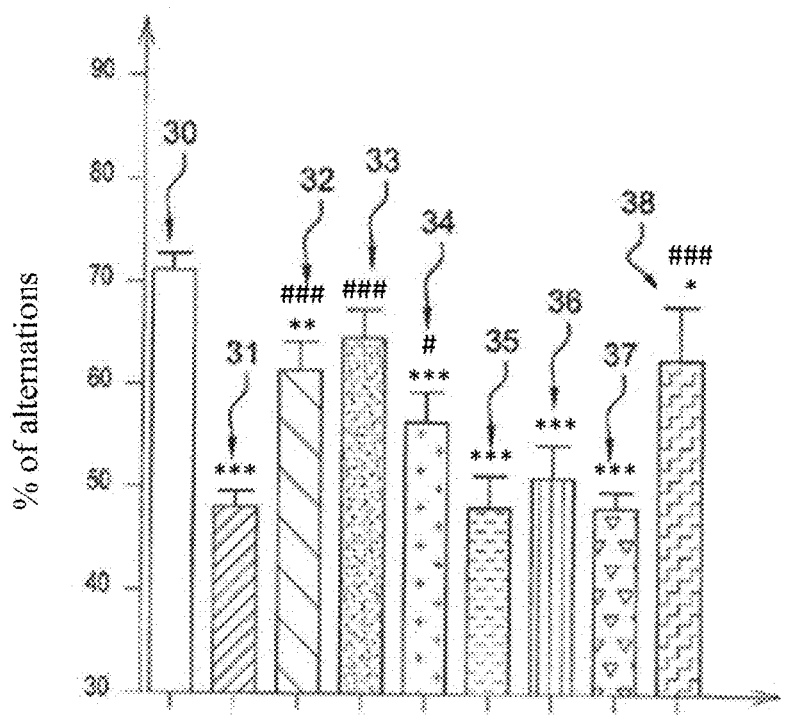
FIG. 11 is a diagram illustrating the alteration of the spontaneous spatial memory of mice injected with amyloid peptide $A\beta_{25-35}$, for mice subjected to irradiation treatment by different devices according to the invention and for control mice not subjected to irradiation treatment.
Figure 17:
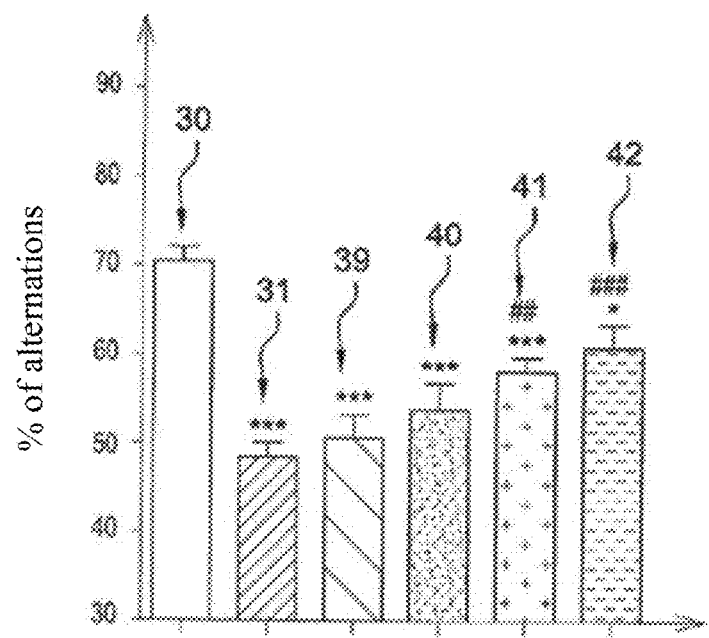

FIG. 17 is, as for FIG. 11, a diagram illustrating the alteration of the spontaneous spatial memory of mice injected with amyloid peptide $A\beta_{25-35}$, for control mice not subjected to irradiation treatment and for mice subjected to irradiation treatment by:
- a device according to the invention comprising irradiation modules provided with light-emitting diodes, pulsed laser and a magnet, by applying treatment times ranging from 2.5 to 10 minutes; and
- a device outside the scope of the invention comprising the same irradiation modules applied only to the user's head.

Figure 12:
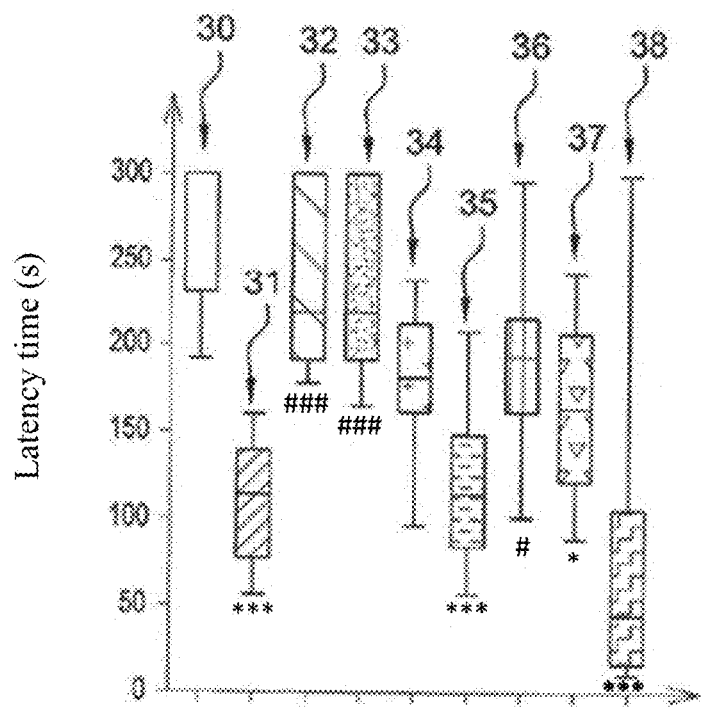
FIG. 12 is a diagram illustrating the alteration of long-term spatial memory according to a first test of mice injected with amyloid peptide $A\beta_{25-35}$, for mice subjected to irradiation treatment by different devices according to the invention and for control mice not subjected to irradiation treatment.
Figure 18:
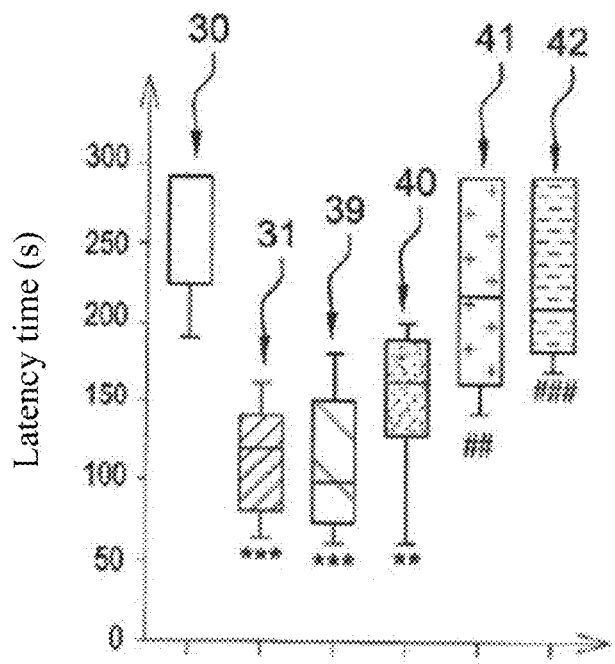

FIG. 18 is, as for FIG. 12, a diagram showing the long-term spatial memory alteration according to a first test of mice injected with amyloid peptide $A\beta_{25-35}$, for control mice not irradiated and for mice irradiated with the same devices as those shown in FIG. 17.

Figure 13:
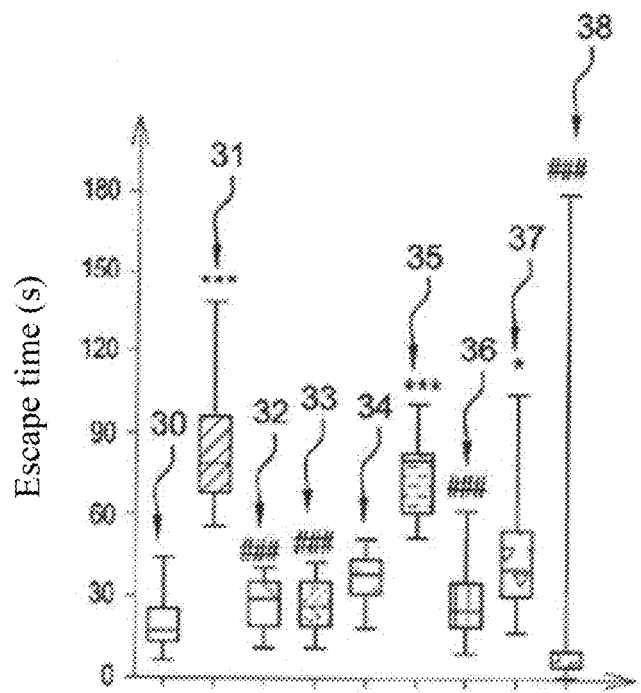
FIG. 13 is a diagram showing the long-term spatial memory alteration according to a second test of mice injected with amyloid peptide $A\beta_{25-35}$, for mice subjected to irradiation treatment by different devices according to the invention and for control mice not subjected to irradiation treatment.
Figure 19:
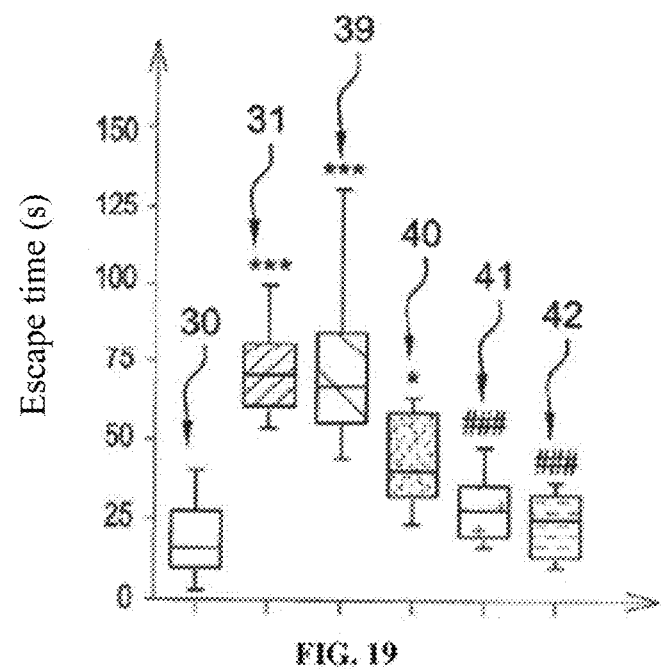

FIG. 19 is, as for FIG. 13, a diagram showing the long-term spatial memory alteration according to a second test of mice injected with amyloid peptide $A\beta_{25-35}$, for control mice not irradiated and for mice irradiated with the same devices as those shown in FIG. 17.

Figure 14:
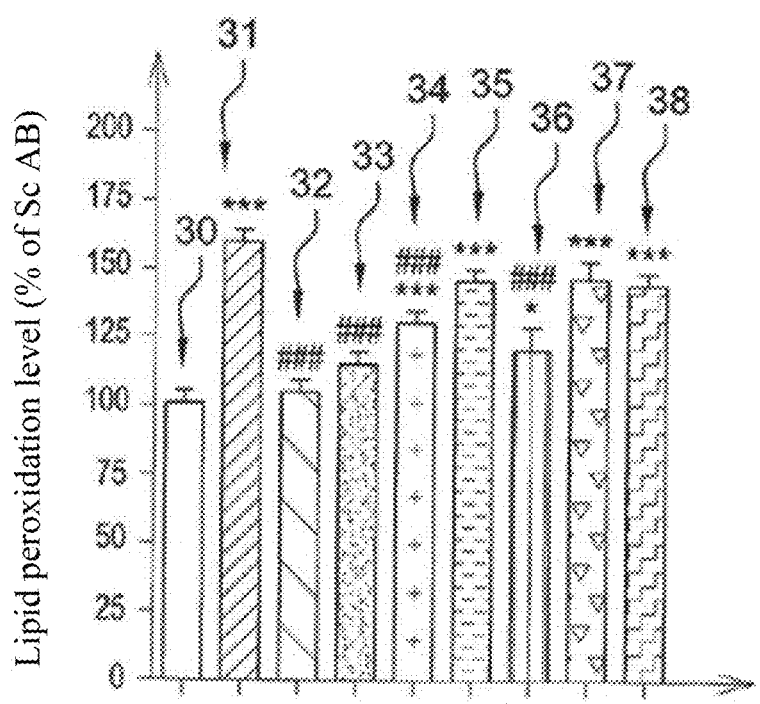
FIG. 14 is a diagram illustrating the level of lipid peroxidation in the hippocampus of mice injected with amyloid peptide $A\beta_{25-35}$, for mice subjected to irradiation treatment by different devices according to the invention and for control mice not subjected to irradiation treatment.
Figure 20:
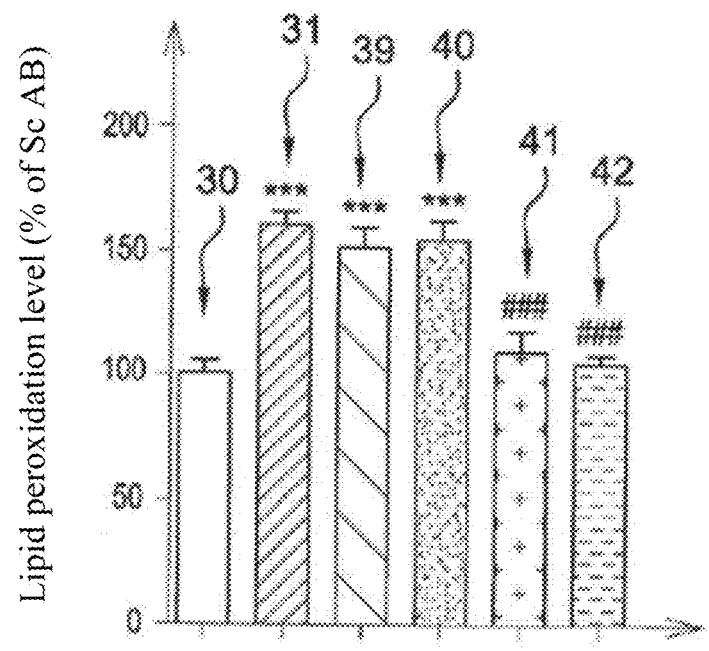

FIG. 20 is, as for FIG. 14, a diagram showing the level of lipid peroxidation in the hippocampus of mice injected with the amyloid peptide $A\beta_{25-35}$, for control mice not subjected to irradiation treatment and for mice subjected to irradiation treatment according to the same devices as those mentioned in FIG. 17.

Figure 15:
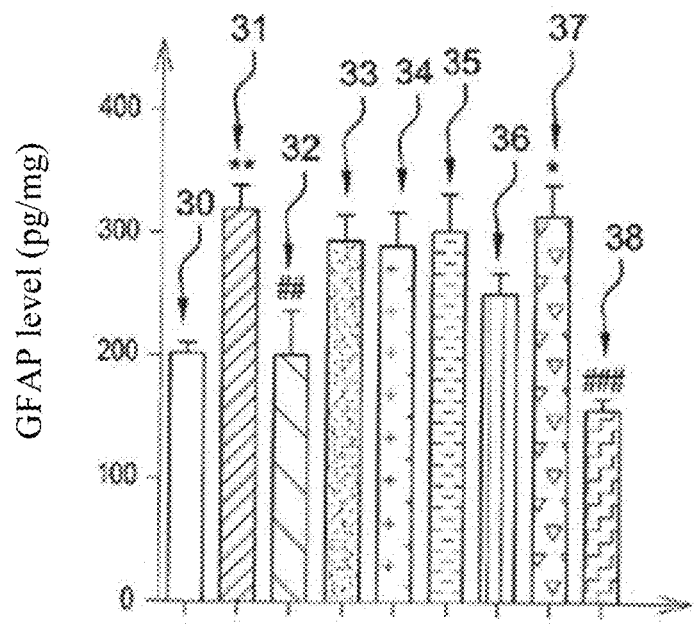
FIG. 15 is a diagram showing the level of glial fibrillary acidic protein (GFAP) measured by ELISA in the hippocampus of mice to which amyloid peptide $A\beta_{25-35}$ was injected, for mice subjected to irradiation treatment by different devices according to the invention and for control mice not subjected to irradiation treatment.
Figure 21:
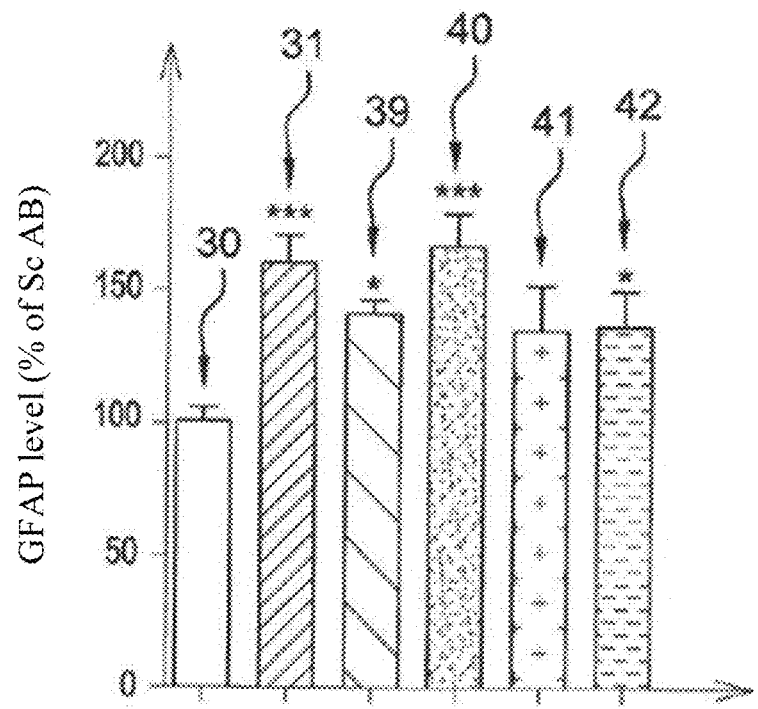

FIG. 21 is, as for FIG. 15, a diagram showing the level of glial fibrillary acidic protein (GFAP) measured by ELISA in the hippocampus of mice to which amyloid peptide $A\beta_{25-35}$ was injected, for control mice not subjected to irradiation treatment and for mice subjected to irradiation treatment using the same devices as those shown in FIG. 17.

Figure 16:
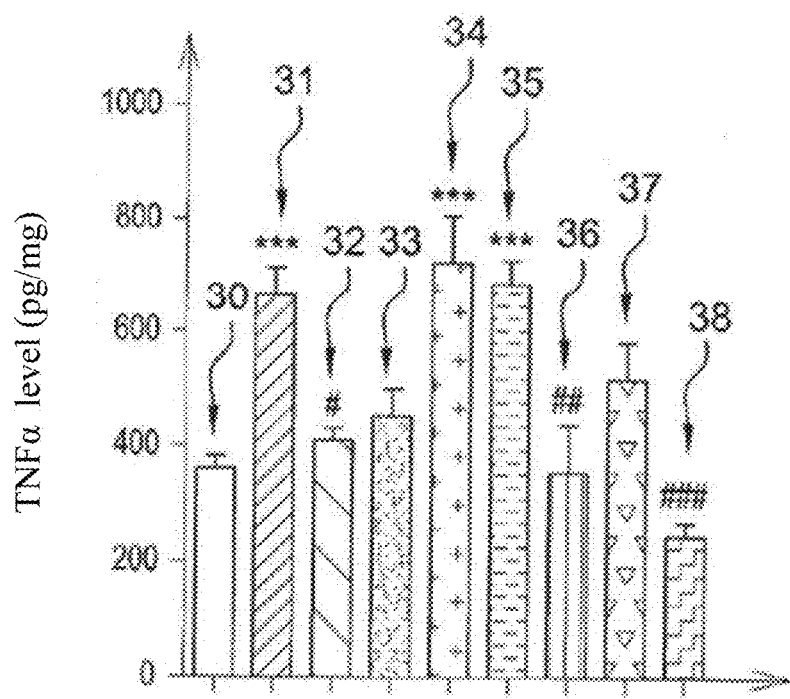
FIG. 16 is a diagram illustrating the level of tumour necrosis factor (TNFα) measured by ELISA in the hippocampus of mice injected with amyloid peptide $A\beta_{25-35}$, for mice subjected to irradiation treatment by different devices according to the invention and for control mice not subjected to irradiation treatment.
Figure 22:
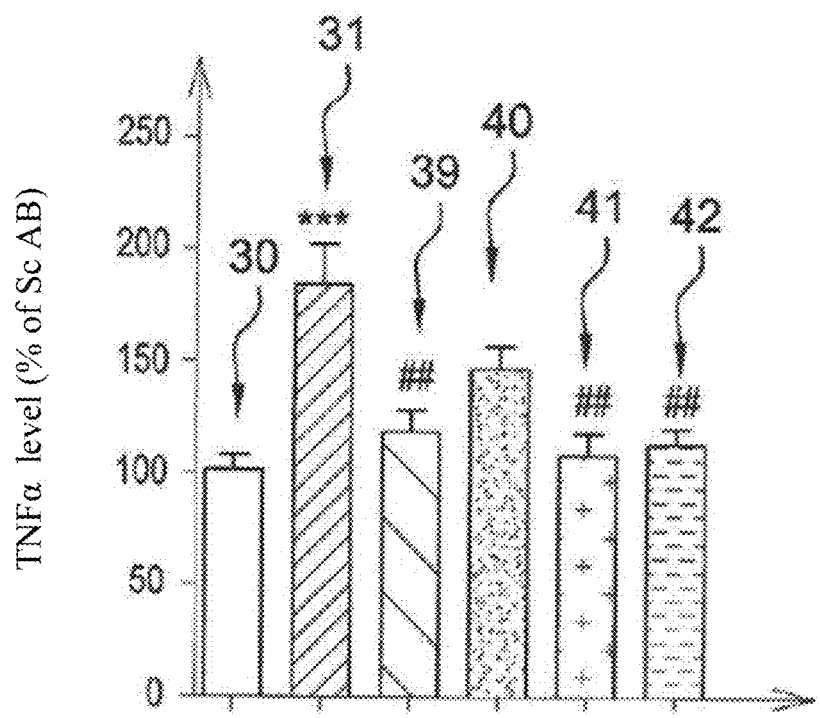

FIG. 22 is, as for FIG. 16, a diagram showing the level of tumour necrosis factor (TNFα) measured by ELISA in the hippocampus of mice to which amyloid peptide $A\beta_{25-35}$ was injected, for control mice not irradiated and for mice irradiated with the same devices as those shown in FIG. 17.

Figure 23:
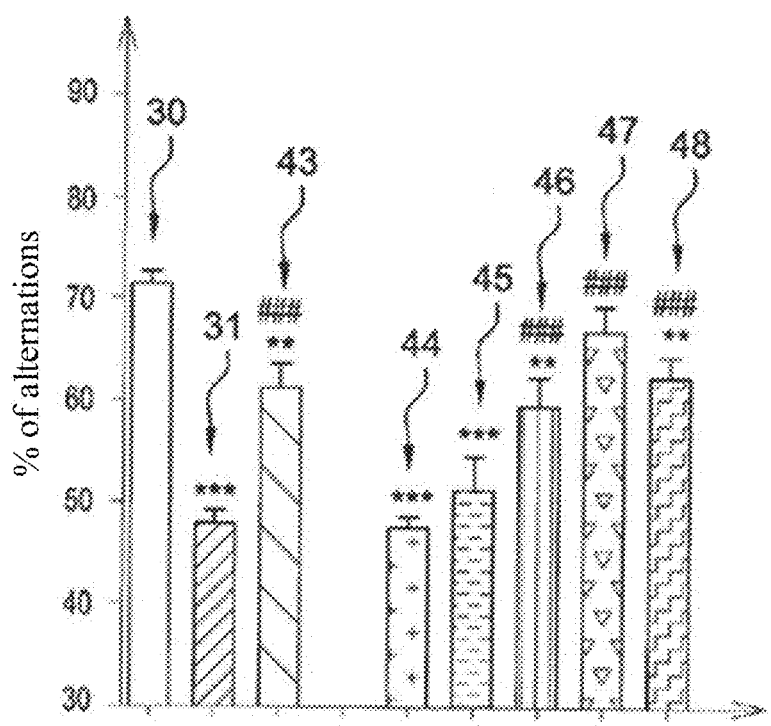

FIG. 23 is, as for FIGS. 11 and 17, a diagram illustrating the alteration of the spontaneous spatial memory of mice to which amyloid peptide $A\beta_{25-35}$ was injected, for control mice not subjected to irradiation treatment and for mice subjected to irradiation treatment by:
- a device according to the invention comprising irradiation modules provided with light-emitting diodes, pulsed laser and a magnet, by applying different irradiation frequencies ranging from 0 to 1000 hertz; and
- devices outside the scope of the invention comprising irradiation modules applied only to the user's head or abdomen.

Figure 24:
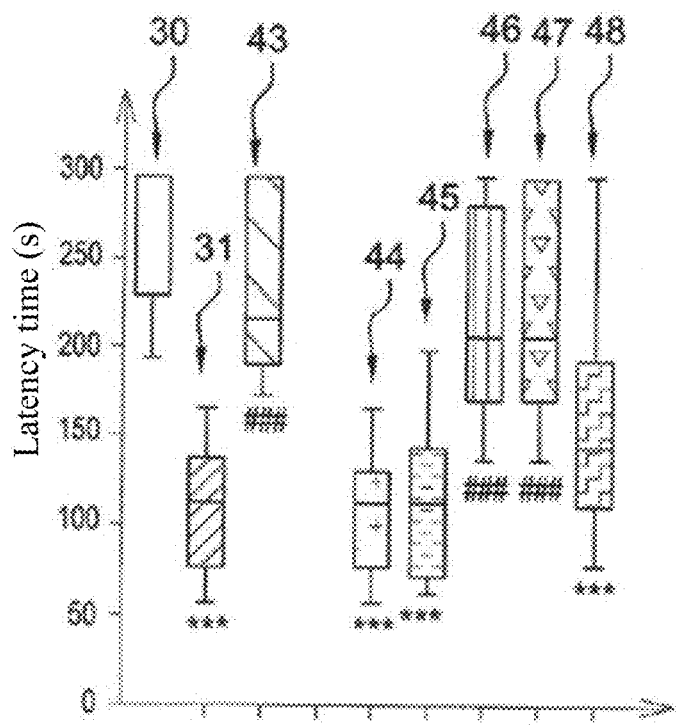

FIG. 24 is, as for FIGS. 12 and 18, a diagram showing the long-term spatial memory alteration according to a first test of mice injected with amyloid peptide $A\beta_{25-35}$, for control mice not irradiated and for mice irradiated with the same devices as those shown in FIG. 23.

Figure 25:
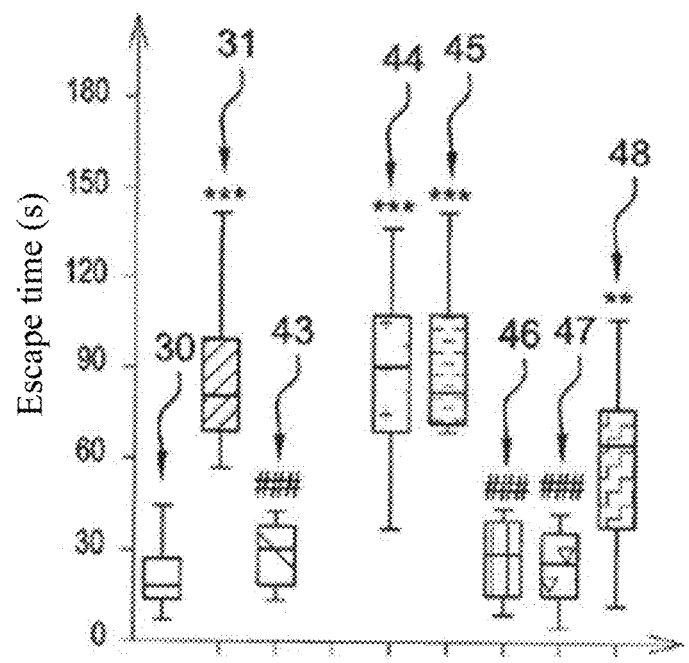

FIG. 25 is, as for FIGS. 13 and 19, a diagram showing the long-term spatial memory alteration according to a second test of mice injected with amyloid peptide $A\beta_{25-35}$, for control mice not irradiated and for mice irradiated with the same devices as those shown in FIG. 23.

Figure 26:
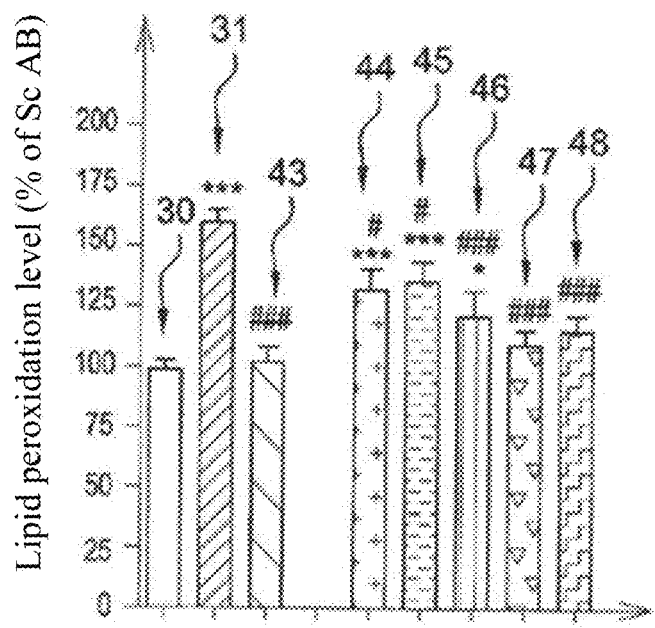

FIG. 26 is, as for FIGS. 14 and 20, a diagram showing the level of lipid peroxidation in the hippocampus of mice injected with amyloid peptide $A\beta_{25-35}$, both for control mice not irradiated and for mice irradiated with the same devices as those shown in FIG. 23.

Figure 27:
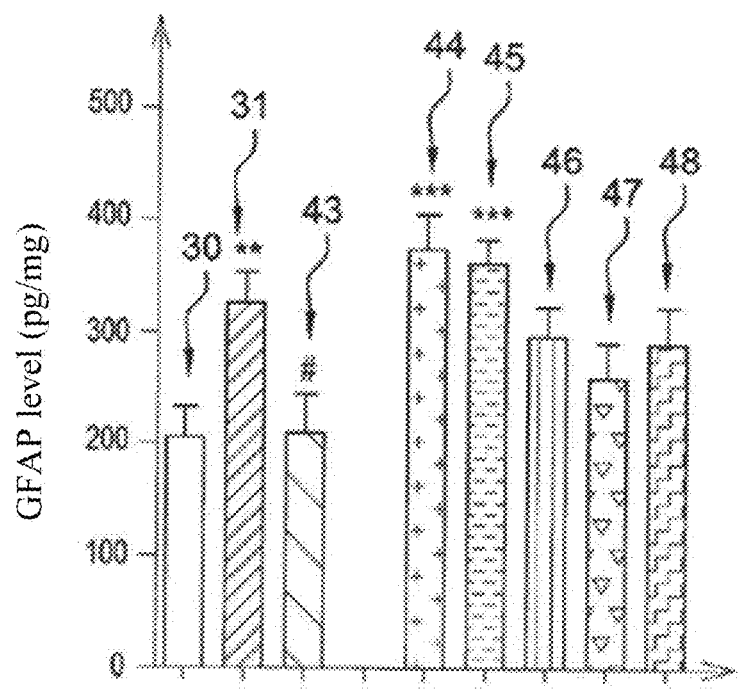

FIG. 27 is, as for FIGS. 15 and 21, a diagram illustrating the level of glial fibrillary acidic protein (GFAP) measured by ELISA in the hippocampus of mice to which amyloid peptide $A\beta_{25-35}$ was injected, for control mice not subjected to irradiation treatment and for mice subjected to irradiation treatment using the same devices as those mentioned in FIG. 23.

Figure 28:
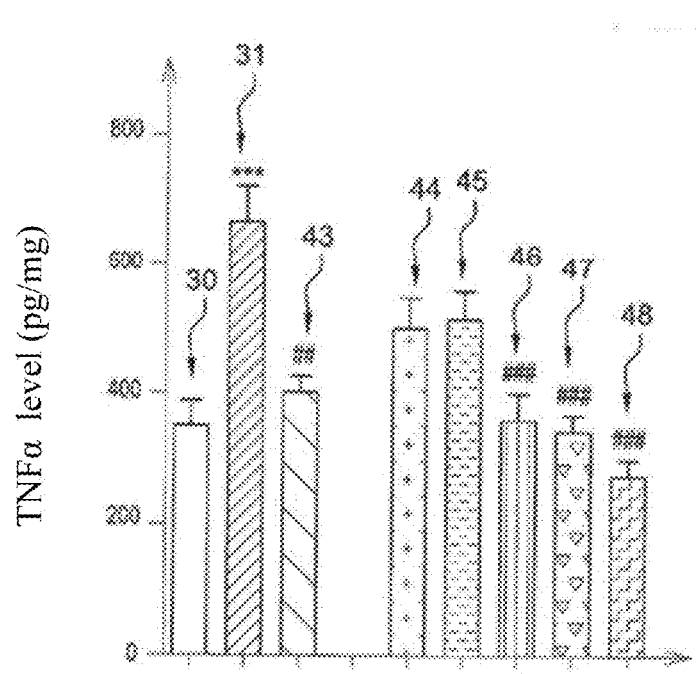

FIG. 28 is, as for FIGS. 16 and 22, a diagram illustrating the level of tumour necrosis factor (TNFα) measured by ELISA in the hippocampus of mice to which amyloid peptide $A\beta_{25-35}$ was injected, for control mice not irradiated and for mice irradiated using the same devices as those shown in FIG. 23.

Figure 29:
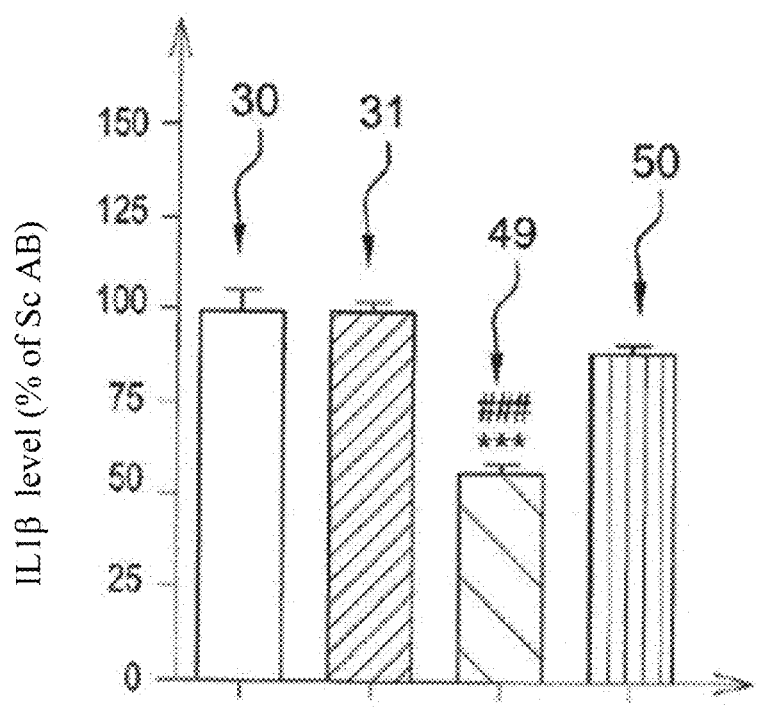

FIG. 29 is a diagram showing the level of interleukin-1 beta (IL-1β) in the frontal cortex of mice injected with amyloid peptide $A\beta_{25-35}\beta$, for control mice not subjected to irradiation treatment and for mice subjected to irradiation treatment by a device according to the invention comprising irradiation modules provided with light-emitting diodes, pulsed laser and a magnet, and to irradiation treatment by an identical device according to the invention but without a magnet.

Figure 30:
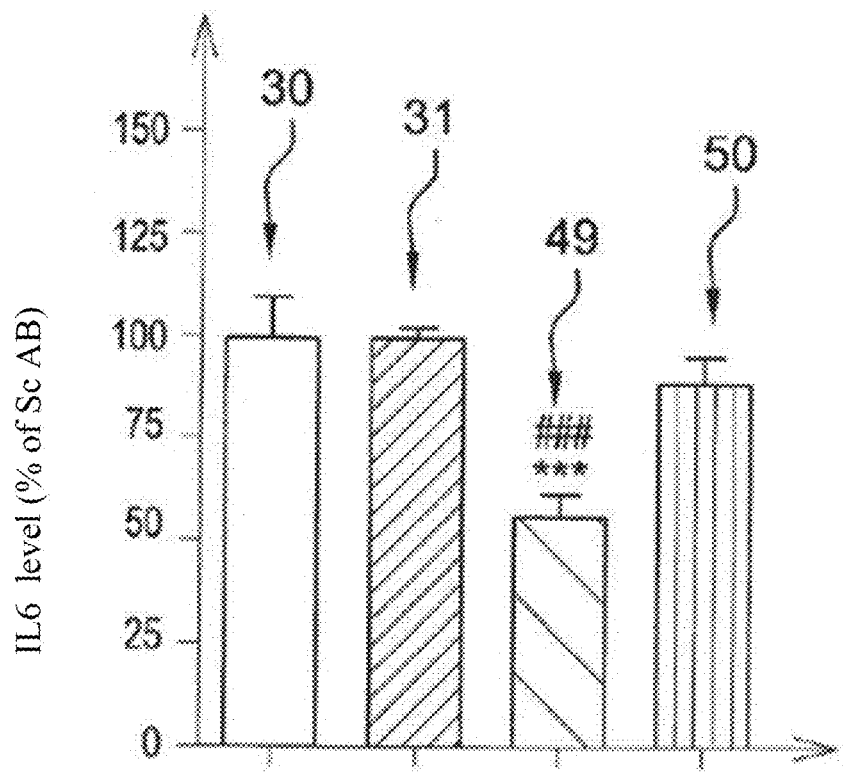

FIG. 30 is a diagram showing the level of interleukin-6 (IL-6) in the frontal cortex of mice injected with amyloid peptide $A\beta_{25-35}$, both for control mice not irradiated and for mice irradiated with the same devices as those shown in FIG. 29.

Figure 31:
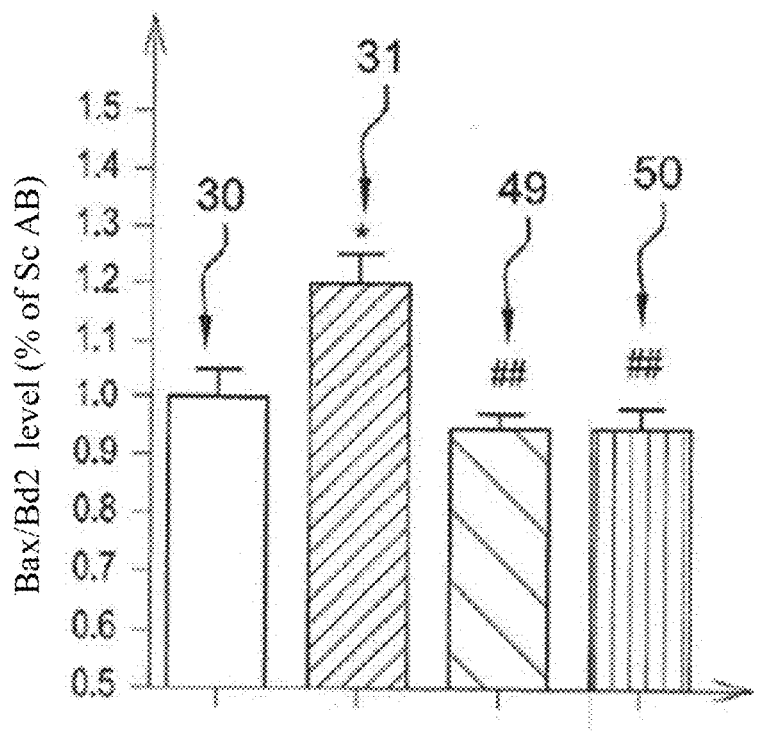

FIG. 31 is a diagram showing the level of Bax/Bcl2 protein in the frontal cortex of mice injected with amyloid peptide $A\beta_{25-35}$, both for control mice not subjected to irradiation treatment and for mice subjected to irradiation treatment using the same devices as those shown in FIG. 29.

Figure 32:
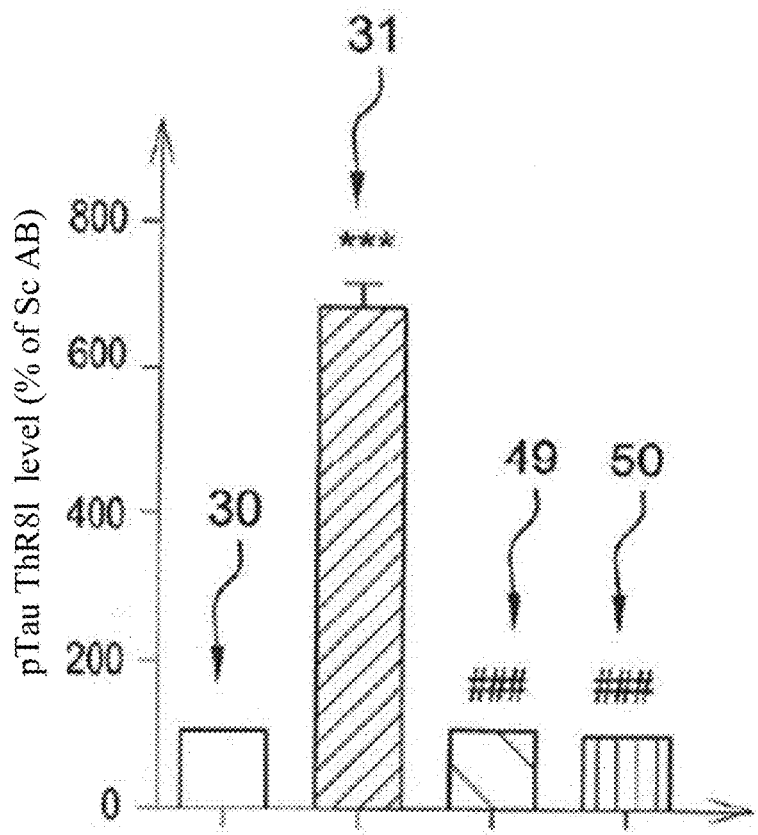

FIG. 32 is a diagram showing the level of phosphorylated tau protein on Thr81 (pTau Thr81) in the frontal cortex of mice to which amyloid peptide $A\beta_{2535}$ was injected, for control mice not subjected to irradiation treatment and for mice subjected to irradiation treatment using the same devices as those shown in FIG. 29.

Figure 33:
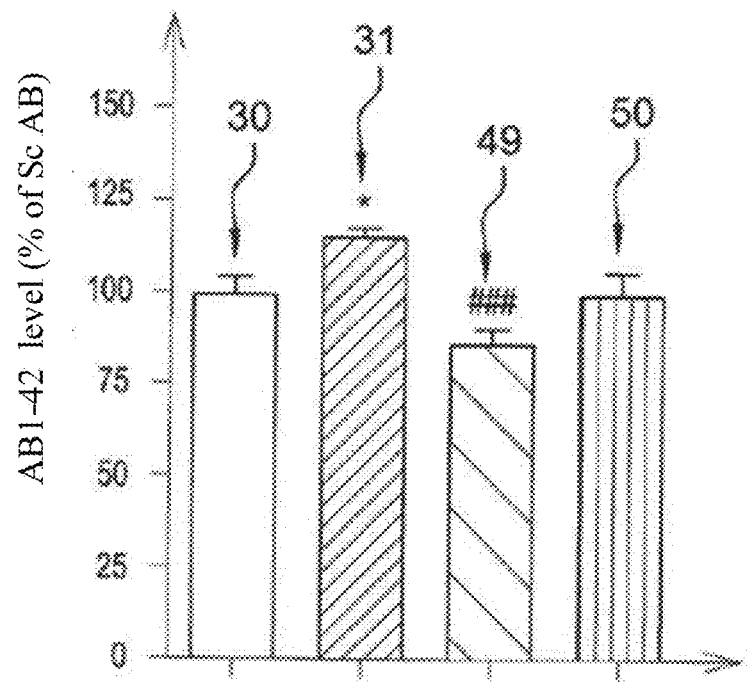

FIG. 33 is a diagram showing the level of amyloid protein-β (1-42) ($A\beta_{1-42}$) in the frontal cortex of mice to which amyloid peptide $A\beta_{2535}$ was injected, for control mice not subjected to irradiation treatment and for mice subjected to irradiation treatment according to the same devices as those referred to in FIG. 29.

Figure 34:
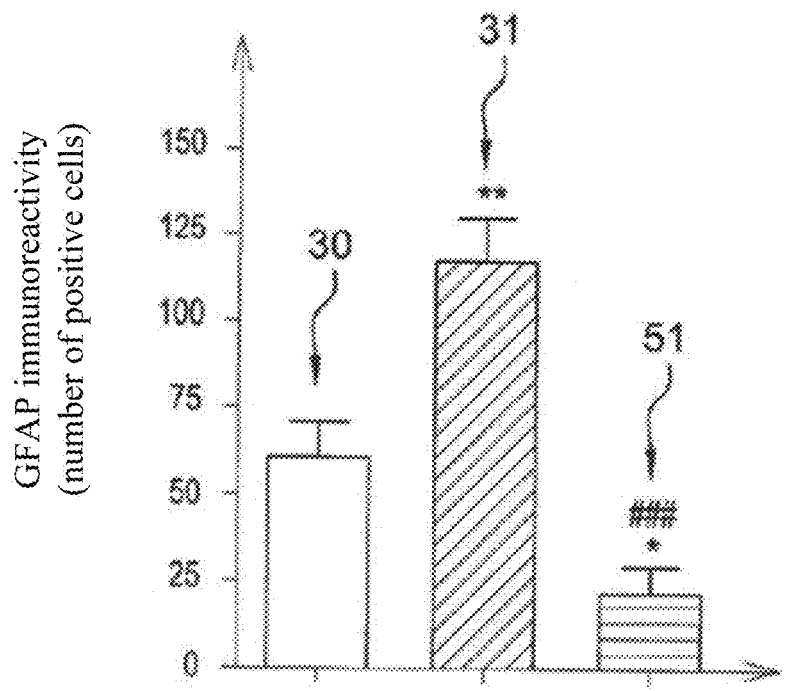

FIG. 34 is a diagram illustrating the activation of astrocytes observed in the CA1 region of the hippocampus in a series of histological sections of mouse brain injected with oligomers $A\beta_{25-35}$, for control mice not subjected to irradiation treatment and for mice subjected to irradiation treatment by a device according to the invention comprising irradiation modules provided with electroluminescent diodes, pulsed laser and a magnet.

Figure 35:
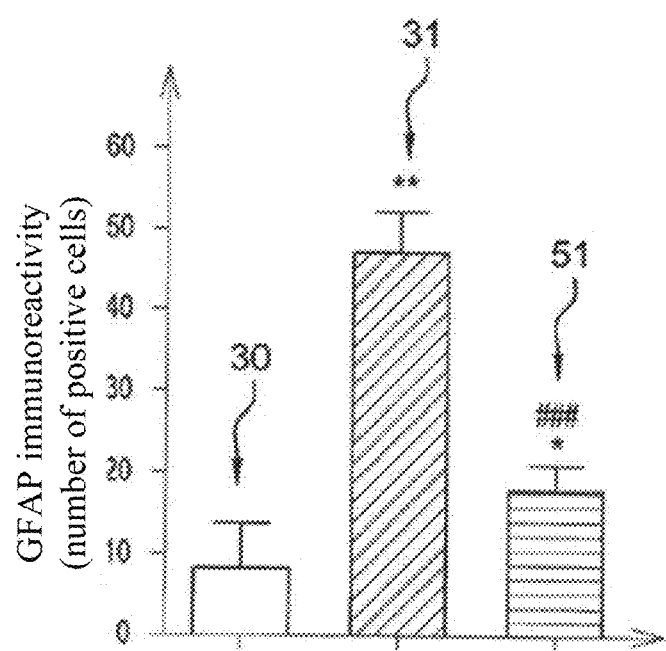

FIG. 35 is a diagram illustrating the number of activated microglial cells observed in the in a series of brain sections in the CA1 region of the hippocampus in a series of histological brain sections of mice injected with oligomers $A\beta_{25-35}$, for control mice not subjected to irradiation treatment and for mice subjected to irradiation treatment by the device referred to in FIG. 34.

Figure 36:
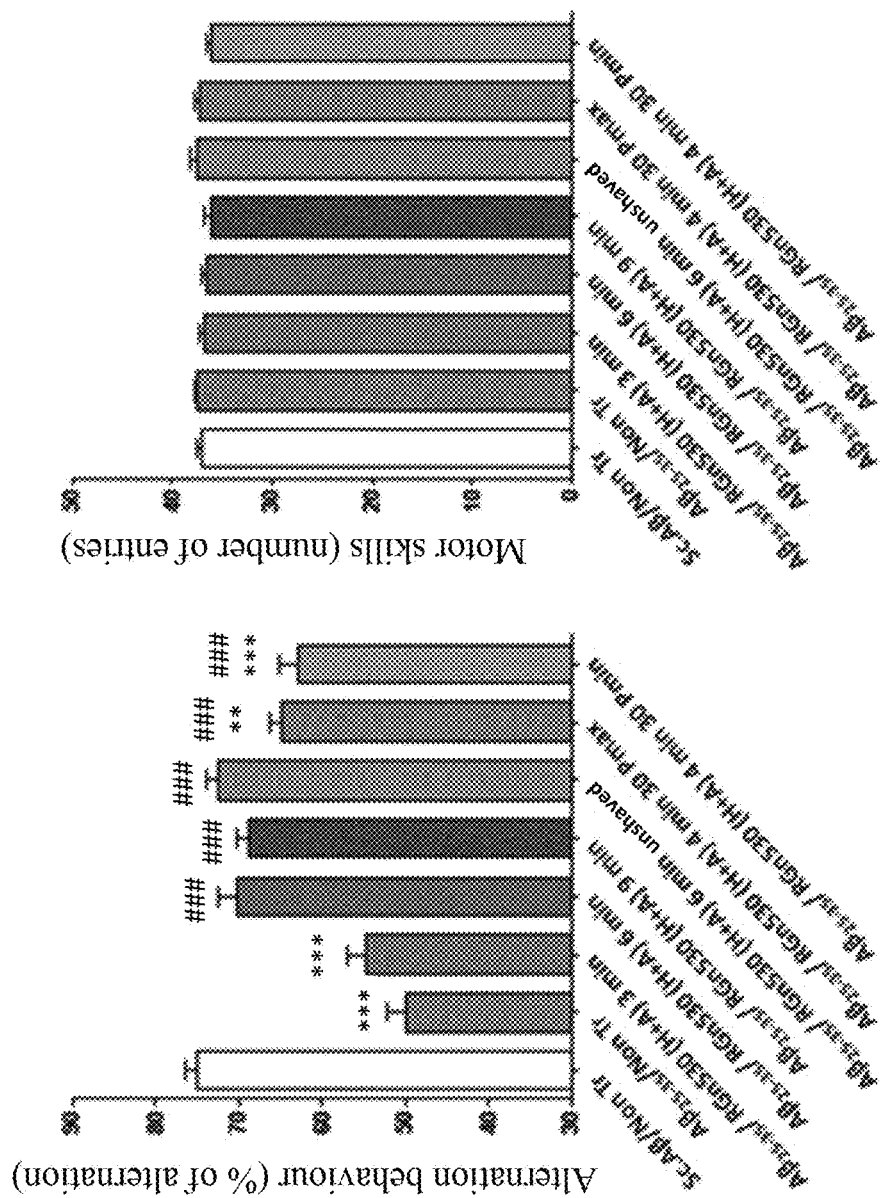

FIG. 36 is a diagram illustrating the short-term spatial memory of mice (Y-maze test). The alternation behaviour of the mice in the tunnel is shown in the diagram on the left and the motor skills of the mice are shown in the diagram on the right. This test was performed on different groups of mice (n=12 mice/group) to which amyloid peptide $A\beta_{25-35}$ or the control peptide (Sc.Aβ) was injected, for control mice not subjected to transcutaneous irradiation treatment and for mice subjected to transcutaneous irradiation treatment using the "RGn530" device. The statistical analysis was performed using Dunn's test with *p<0.05, p<0.01, *p<0.0001 (analysis against the control peptide (Sc.$A\beta_{25-35}$) group/untreated) and #p<0.05, ##p<0.01, ###p<0.0001 (analysis against the amyloid peptide $A\beta_{25-35}$ group)/untreated).

Figure 37:
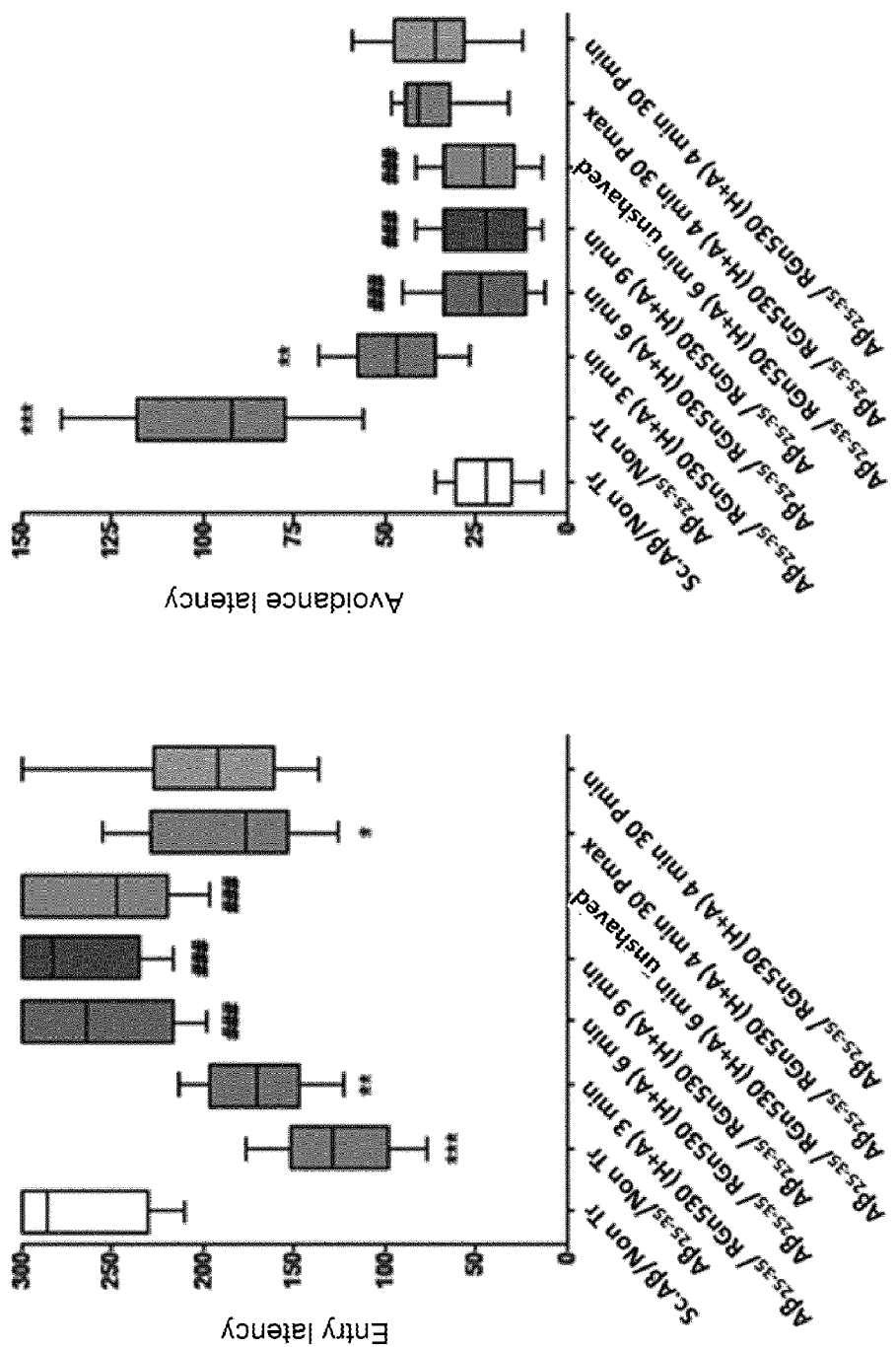

FIG. 37 is a diagram illustrating the long-term contextual memory of mice (passive avoidance test). The latency time of mouse entry into the tunnel is shown in the left diagram and the latency time of mouse avoidance is shown in the right diagram. This test was performed on different groups of mice (n=12 mice/group) to which amyloid peptide $A\beta_{2535}$ or the control peptide (Sc.Aβ) was injected, for control mice not subjected to irradiation treatment and for mice subjected to transcutaneous irradiation treatment using the "RGn530" device. The statistical analysis was performed using Dunn's test with *p<0.05, p<0.01, *p<0.0001 (analysis against the control peptide (Sc.$A\beta_{25-35}$) group/vehicle (distilled water)) and #p<0.05, ##p<0.01, ###p<0.0001 (analysis against the amyloid peptide $A\beta_{25-35}$ group)/vehicle (distilled water).

Figure 38:
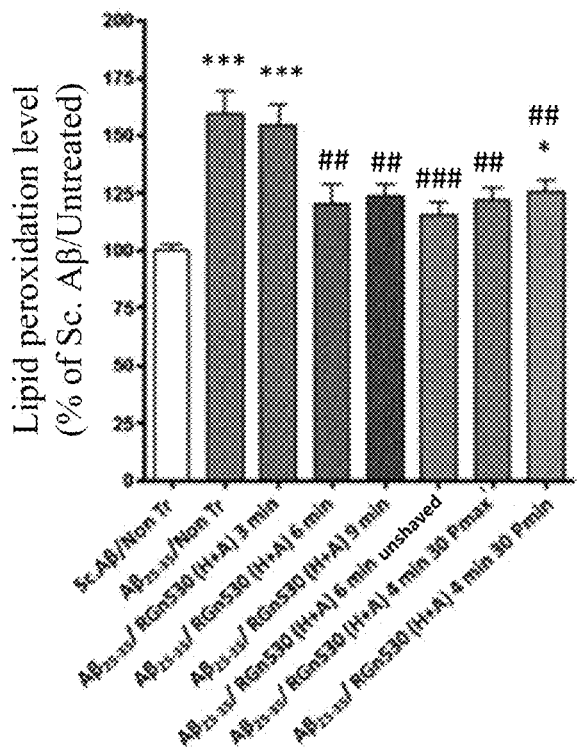

FIG. 38 is a diagram showing the level of lipid peroxidation in the hippocampus of mice (n=12 mice per group) to which amyloid peptide $A\beta_{25-35}$ or control peptide (Sc.Aβ) was injected, for control mice not subjected to irradiation treatment and for mice subjected to transcutaneous irradiation treatment using the "RGn530" device. The statistical analysis was performed using Dunn's test with *p<0.05, p<0.01, *p<0.0001 (analysis against the control peptide (Sc.$A\beta_{25-35}$) group/vehicle (distilled water)) and #p<0.05, ##p<0.01, ###p<0.0001 (analysis against the amyloid peptide ($A\beta_{25-35}$) group/vehicle (distilled water)).

Figure 39:
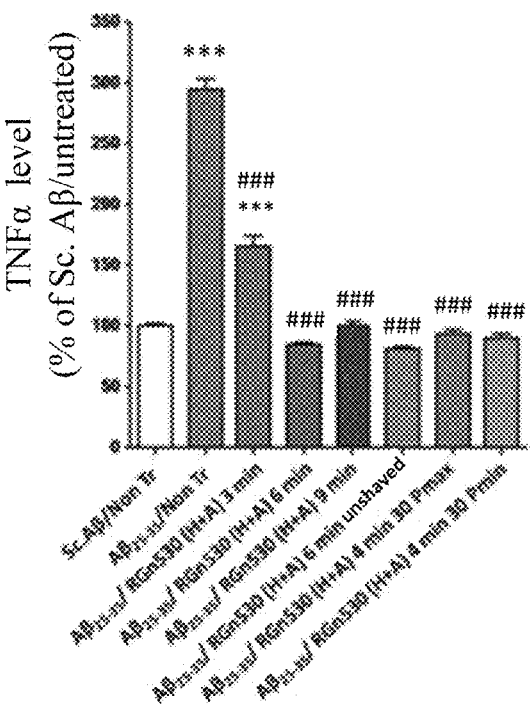

FIG. 39 is a diagram illustrating the level of tumour necrosis factor (TNFα) measured by ELISA in the hippocampus of mice (n=12 mice per group) to which amyloid peptide $A\beta_{25-35}$ or control peptide was injected, for control mice not subjected to irradiation treatment and for mice subjected to transcutaneous irradiation treatment using the "RGn530" device. The statistical analysis was performed using Dunn's test with *p<0.05, p<0.01, *p<0.0001 (analysis against the control peptide (Sc.$A\beta_{25-35}$) group/vehicle (distilled water)) and #p<0.05, ##p<0.01, ###p<0.0001 (analysis against the amyloid peptide ($A\beta_{25-35}$) group/vehicle (distilled water).

Figure 40:
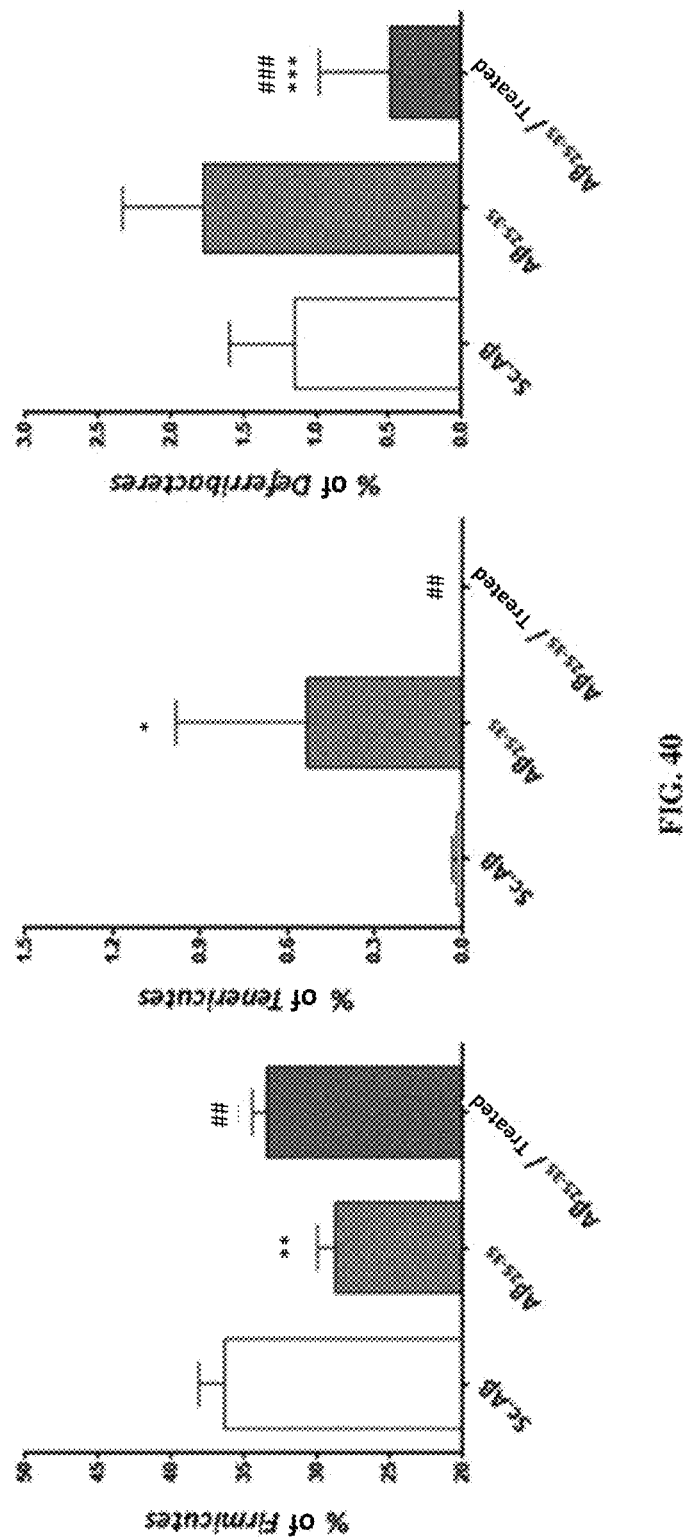

FIG. 40 is a diagram illustrating the abundance of three bacterial phyla (Firmicutes, Tenericutes and Deferribacteres) analysed by 16S rDNA in the caecum of mice (n=12 mice per group) to which the control peptide (Sc.$A\beta_{25-35}$) or the amyloid peptide $A\beta_{25-35}$ was injected without irradiation treatment, and mice to which amyloid peptide $A\beta_{25-35}$ was injected and treated by transcutaneous irradiation using the "RGn530" device (6 minutes, shaved mouse). The statistical analysis was performed using the Mann-Whitney test with *p<0.05, p<0.01, *p<0.0001 (untreated amyloid peptide $A\beta_{25-35}$ group versus control (Sc.$A\beta_{25-35}$) group) and #p<0.05, ##p<0.01, ###p<0.0001 (treated amyloid peptide $A\beta_{2535}$ group vs. control (Sc.$A\beta_{25-35}$) group).

DETAILED DESCRIPTION OF THE INVENTION

The Irradiation Device

Figure 1:
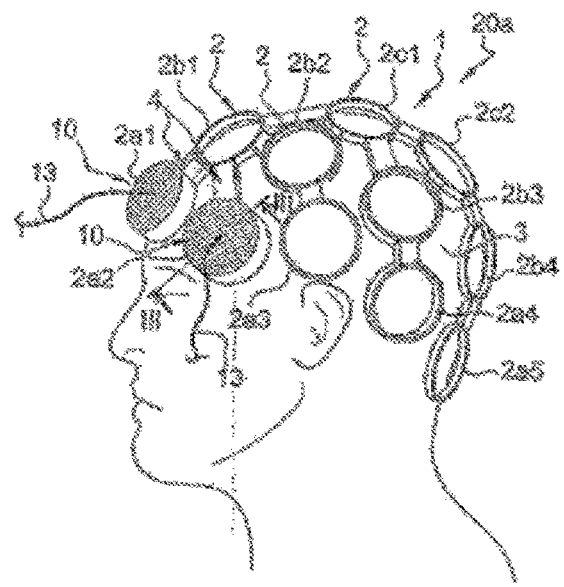
FIG. 1 is a schematic side view of the top portion of the device of the invention positioned on the user's head and comprising, in this example, four irradiation modules (only two of which are visible in this figure).
Figure 2:
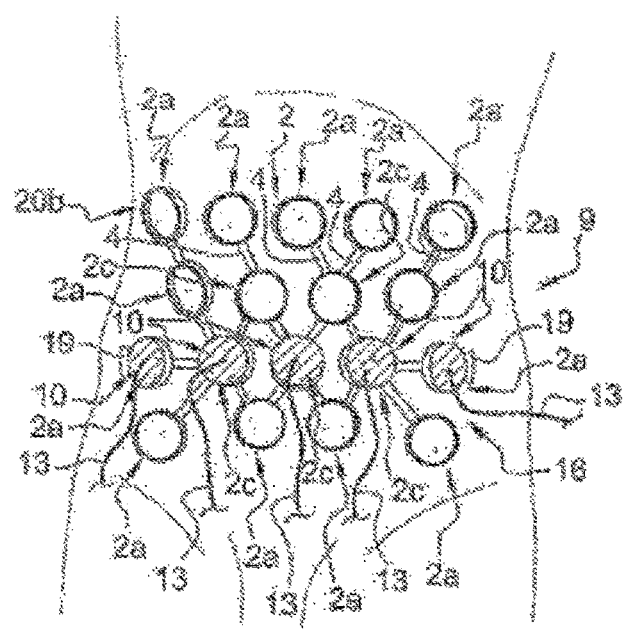
FIG. 2 is a schematic front view of the bottom portion of the device of the invention positioned on the user's abdomen and comprising in this example four irradiation modules.
Figure 3:
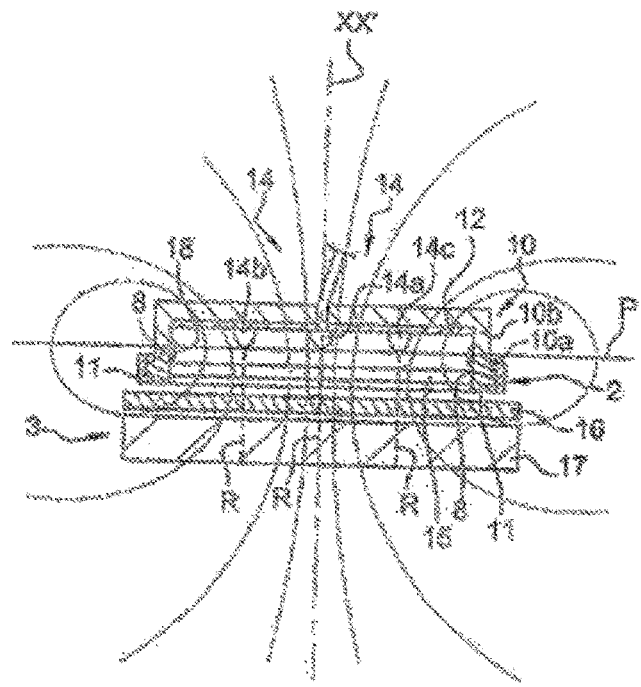
FIG. 3 is a cross-sectional view according to line III-III of FIG. 1 of an irradiation module of the device of the invention according to a first variant, positioned on the skin of a user's head or abdomen.

With reference to FIGS. 1, 2 and 3, the transcutaneous irradiation device of the invention consists of two portions. A first top portion 1 comprises one or a plurality of transcutaneous irradiation modules 10 for positioning on the user's head 3; and a second bottom portion 9 also comprises one or a plurality of transcutaneous irradiation modules 10 for positioning on the user's abdomen 16.

For the purposes of the present invention, "positioned" means that the modules are affixed to the user's skin. For the top portion of the device, the modules are attached to the user's head, and for the bottom portion of the device, the modules are attached to the user's abdomen.

Each transcutaneous irradiation module 10 comprises one or a plurality of irradiation means 14 which may take the form of pulsed type laser sources 14a (preferably a laser diode or any other source of laser radiation known to the skilled person) generating a beam emitting in the infrared spectrum, light-emitting diodes (LEDs) or laser sources generating a beam emitting in the visible spectrum 14b and/or light-emitting diodes (LEDs) generating a beam emitting in the infrared spectrum 14c; as well as possibly means for generating a static, preferably circular, magnetic field, such as a magnet 18 positioned within each transcutaneous irradiation module 10.

As shown in FIG. 1 and for this embodiment, the top portion of the device 1 comprises four transcutaneous irradiation modules 10 (only two of which are visible in this figure) symmetrically arranged forward of the head 3 to reach the frontal lobe. There may be fewer transcutaneous irradiation modules 10 (at least one according to the invention) located in any area of the brain, or conversely, more transcutaneous irradiation modules 10 positioned to reach the frontal lobe, parietal lobe, cerebellum and/or occipital lobe. Preferably, the number of transcutaneous irradiation modules 10 is greater than eight, ten, twelve, fourteen, sixteen, eighteen or twenty, and may be more than twenty-two according to the embodiment of FIGS. 1 and 5 to 10. Preferably, the transcutaneous irradiation modules 10 are in an even number and are distributed symmetrically over the surface of the user's head 3.

As shown in FIG. 2, the bottom portion of the device 9 includes five transcutaneous irradiation modules 10 positioned symmetrically and aligned substantially horizontally on the user's abdomen 16. The area of the abdomen covered by the device of the present invention extends vertically from the groin to the stomach and horizontally over the width of the abdomen. Thus, as for the top portion 1, there may be fewer transcutaneous irradiation modules 10 (at least one according to the invention) located in any area of the abdomen 16, or conversely, a plurality of transcutaneous irradiation modules 10 covering all or part of the abdomen 16 as previously defined. Preferably, the number of transcutaneous irradiation modules 10 is greater than eight, ten, twelve, fourteen or sixteen, and may be eighteen according to the embodiment of FIGS. 1 and 5 to 10. It is also possible to provide a greater number of transcutaneous irradiation modules 10 (for example, a number of transcutaneous irradiation modules 10 greater than eighteen, twenty, twenty, twenty-two or more) may be provided by adapting the bottom portion of the device 9 to a greater number of transcutaneous irradiation modules 10. Preferably, the transcutaneous irradiation modules 10 are in an even number and are distributed symmetrically over the surface of the user's abdomen 16.

FIG. 3 illustrates a section of a transcutaneous irradiation module 10 positioned on the user's head 3, but also applies to a transcutaneous irradiation module 10 positioned on the abdomen 16. Each transcutaneous irradiation module 10 has a general cylindrical shape to ensure the coaxial holding of the transcutaneous irradiation module 10 in a ring 2 forming part of a module support which will be described in detail below. This coaxial configuration is important because it ensures the positioning and fixed maintenance of the transcutaneous irradiation module 10 in the axis of the dedicated ring 2, which cannot be the case when the module is presented, as in the prior art, in the form of a probe equipped with a handle and cables connected to a control and power supply device, the ring then forming in this case only the position indicator function.

The ring 2 is made of a flexible and/or elastic material and has an inner groove 8 in which a corresponding circular rib 11 is inserted on the outer surface of the transcutaneous irradiation module 10 to ensure the fixed and precise positioning of the transcutaneous irradiation module 10 in the axis of the ring 2. The structure of the ring 2 and its coupling means with the transcutaneous irradiation module 10 may differ from those shown in FIG. 3 without leaving the scope of the invention.

In an embodiment, the transcutaneous irradiation module 10 includes an electronic board 12 electrically powered via an electrical cable 13 that extends outside the transcutaneous irradiation module 10. This electrical cable 13 is also shown for each transcutaneous irradiation module 10 in FIGS. 1 and 2. In an alternative embodiment, the rings 2 are connected to each other by a single power cable 13 which opens at each ring 2 by means known to the skilled person in order to automatically supply each transcutaneous irradiation module 10 positioned on a corresponding ring 2. The electrical cable 13 also contains data wires (for example, CAN bus type), a power wire for the irradiation source(s) and one or more ground wires.

Figure 4:
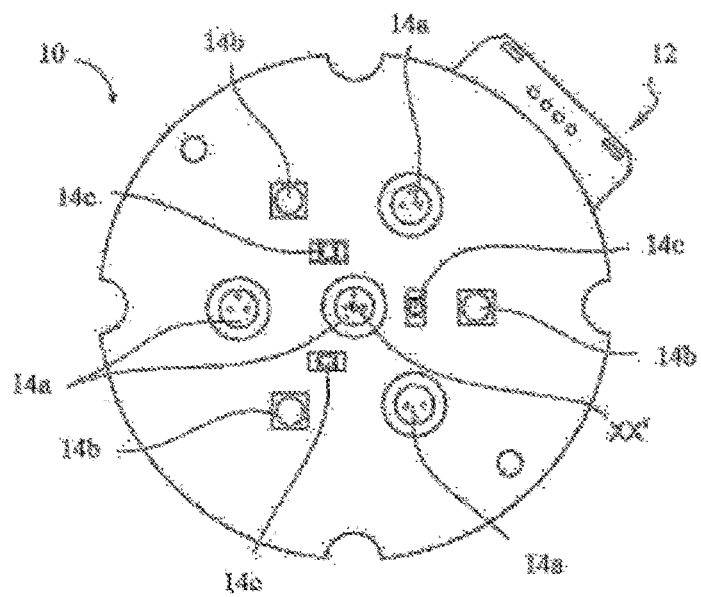
FIG. 4 is a topical representation of the electronic board of an irradiation module of the device of the invention according to a second variant, illustrating the position and quality of the irradiation sources.

According to the two embodiments represented in FIGS. 3 and 4, each transcutaneous irradiation module 10 of the device of the invention includes irradiation sources consisting of at least one pulsed laser 14a generating a beam emitting in the infrared spectrum, at least one light-emitting diode (LED) 14b generating a beam emitting in the red spectrum and at least one light-emitting diode (LED) 14c generating a beam emitting in the infrared spectrum. Alternatively, one or more laser sources 14b generating a beam emitting in the red spectrum may be used instead of or in combination with one or more light-emitting diodes 14b generating a beam emitting in the red spectrum.

For the embodiment shown in FIG. 3, the transcutaneous irradiation module 10 comprises a pulsed laser 14a which is arranged in the main axis XX' of the transcutaneous irradiation module 10, and two LEDs generating a beam emitting respectively in the red and infrared spectrum 14b, 14c which are symmetrically located on either side of the pulsed laser 14a.

In the second preferential embodiment shown in FIG. 4, the transcutaneous irradiation module 10 includes four pulsed lasers 14a, three light-emitting diodes generating a beam emitting in the red spectrum 14b and three light-emitting diodes generating a beam emitting in the infrared spectrum 14c.

The irradiation sources 14 are thus divided into three groups, namely more precisely:

at least one, preferentially two, even more preferentially three or more light-emitting diodes (LEDs) generating a beam emitting in the infrared spectrum 14c, said beam having a wavelength between 700 and 1200 nanometres, preferably between 800 and 900 nanometres, preferably about 850 nanometres. The LEDs 14c are circular and evenly distributed around and near the main axis XX' of the module;

at least one, preferentially two, even more preferentially three or more light-emitting diodes (LEDs) generating a beam emitting in the red spectrum 14b, said beam having a wavelength between 600 and 700 nanometres, preferably about 640 nanometres or preferably about 625 nm. The LEDs 14b are circularly and evenly distributed around and at a greater distance than the LEDs 14c on the main axis XX'; and at least one, preferentially two, even more preferentially three, even more preferentially four or more pulsed laser sources (preferably laser diodes) 14a generating a beam emitting in the infrared spectrum, said beam having a wavelength between 700 and 1200 nanometres, preferably between 800 and 900 nanometres, preferably about 850 nanometres. In an embodiment, each of these laser sources 14a has a pulse train comprising:

a pulse duration between 20 and 200 nanoseconds;
a pulse train repetition frequency between 1 and 25 kHz inclusive, preferably between 10 and 15 kHz inclusive, preferably 15 kHz or preferably 10 kHz;
an impulse power of between 0.5 and 12 watts, preferably between 1 and 7 watts inclusive; and
a voltage between 2 and 5 volts inclusive, preferably 4.24 volts±10% or preferably 2.30 volts±10%.

In an embodiment, a first laser source 14a is centred on the axis XX' and the other three laser sources are circularly and evenly distributed around and at a greater distance than the LEDs 14c of the main axis XX', on the same circumference as the LEDs 14b. In an alternative embodiment, three laser sources 14a are circularly and evenly distributed around the axis XX'. In an alternative embodiment, less than three laser sources 14a, for example, a single laser source 14a is centred on the axis XX' or off-centre on the axis XX'.

Within the scope of the invention, the laser sources and the LEDs can be arranged in the main axis XX' or offset, what is essential is that the illumination is carried out in the direction of the surface (head or abdomen) to be irradiated.

In a preferential embodiment, the transcutaneous irradiation module 10 also includes means not represented but known to the skilled person providing a pulsed mode, or in other words, an "overall modulation frequency" applied to the light-emitting diodes 14b, 14c and to the laser sources 14a. In an embodiment, the overall modulation frequency is between 0 and 4000 Hz, preferably between 1 and 1000 Hz, preferably between 1 and 100 Hz, preferably around 10 Hz.

In the latter preferential embodiment, an identical overall modulation frequency is applied to the irradiation sources 14a, 14b, 14c of the transcutaneous irradiation modules 10 applied to the user's head 3 and to the irradiation sources 14a, 14b, 14c of the transcutaneous irradiation modules 10 applied to the user's abdomen 16. Thus, in an embodiment, an overall modulation frequency between 0 and 4000 Hz, preferably between 1 and 1000 Hz, preferably between 1 and 100 Hz, preferably between 1 and 100 Hz, preferably about 10 Hz is applied to the irradiation sources 14a, 14b, 14c of the transcutaneous irradiation modules 10 applied to the user's head 3; and an identical overall modulation frequency is applied to the irradiation sources 14a, 14b, 14c of the transcutaneous irradiation modules 10 applied to the user's abdomen 16.

Alternatively, it may be provided that the top portion 1 of the device is subjected to a given overall modulation frequency (for example, 10 hertz), and the bottom portion 9 of the device is subjected to a different overall modulation frequency (for example, 1000 hertz).

"Overall modulation frequency" means the establishment of an alternation of non-illuminated and illuminated ranges. In the non-limiting exemplary embodiments, the illuminated ranges are of equal duration to the duration of the non-illuminated ranges. This overall modulation frequency is configured by a computer-controlled electronic control console to apply a controlled transmission frequency.

Advantageously, each transcutaneous irradiation module 10 comprises a magnet 18 which extends in a plane P and is positioned to generate a static magnetic field, preferably circular, between 20 and 2000 milliteslas, preferably between 100 and 1000 milliteslas, preferably around 200 milliteslas. The magnet 18 is circular in shape and is attached to the inner side of the transcutaneous irradiation module 10. The light rays R generated by the laser source 14a, the light-emitting diode (LED) 14b and the light-emitting diode (LED) 14c therefore extend perpendicular to the plane P of the magnet 18 and inside this magnet 18.

Concerning the laser source 14a, preferably the laser diode 14a, it is thus subjected to a double pulse:

the first pulse, intrinsic, has a pulse train comprising a repetition frequency between 1 and 25 kHz inclusive, preferably between 10 and 15 kHz inclusive, preferably 15 kHz or preferably 10 kHz; and
the second pulse, extrinsic, and also applicable to the LEDs 14b and 14c, comprising a repetition frequency between 0 and 4000 Hz, preferably between 1 and 1000 Hz, preferably between 1 and 100 Hz, preferably around 10 Hz.

Electromagnetic radiation generated by the irradiation sources 14a, 14b, 14c pass through an optical guide 15 located in the bottom portion of the transcutaneous irradiation module 10 near the hair 16 and skin 17 of the patient's head 3 (or near the abdomen 16). The radiation then enters the targeted area of the brain or abdomen.

The transcutaneous irradiation module 10 can be made in one piece, or in two pieces as shown in FIG. 3. In the latter case, the transcutaneous irradiation module 10 comprises an annular bottom portion 10a, and an annular top portion 10b. The bottom 10a and top 10b portions may be assembled by any means known to the skilled person, in particular by a bayonet system, by screwing or by snap-fitting. Remaining within the scope of the invention, the structure of the module may be different and adapted by the skilled person.

As shown in FIG. 3 for this particular embodiment, the circular rib 11 is arranged on the bottom portion 10a which includes the optical guide 15, so that this bottom portion 10a can remain in place on the ring 2 between two treatments. The top portion 10b includes the electronic board and the irradiation source(s) and can be positioned on the bottom portion at the time of treatment.

Module Support

To ensure the fixed and precise positioning of the transcutaneous irradiation modules 10 applied to the head 3 or the abdomen 16, it is provided that the module(s) be arranged on a module support comprising one or more rings made of a flexible and/or elastic material making it possible to ensure by elastic grip the fixed maintenance of a transcutaneous irradiation module. Flexible and/or elastic material means a material such as elastomer or rubber which allows the insertion of a substantially cylindrical outer surface modulus into the ring by spacing the said ring and elastic return against the modulus. The material can be flexible without being elastic, its spacing for inserting and fixing the module implying a significant extension of the material, the module can then be held in the ring by friction. The support also includes means of positioning on the area to be irradiated. These means may take the form of a strap, but may also, or in addition, be in the shape of the support which, by resting on the area to be treated, adapts to that area and is held in place by means of this adapted support shape.

The module support 20a for the top portion 1 of the device of the invention must adapt to the shape of the head 3. FIGS. 5 to 10 are used to describe the module support of the invention applied to neurological treatments. This module support is structurally adapted to the construction of the module support 20b for the abdomen.

The support 20a includes a plurality of rings 2 for holding transcutaneous irradiation modules 10 distributed on the surface of the head 3 (for clarity reasons, not all rings are referenced in the figures). As an example, each ring is made of silicone, with an external radius of 25 millimetres, an internal radius of 23 millimetres (i.e. 2 millimetres thick), and a height of 6 millimetres. The height must be sufficient to hold a module that will be described below. As an alternative to the use of silicone, the rings may be made of rubber, elastomeric material or any other polymeric or nonpolymeric material which is flexible enough to allow the insertion and retention of an essentially cylindrical outer surface module.

The rings 2 are symmetrically distributed on the support, so that when they are positioned on the head 3, the symmetry axis of the support XX' coincides with the centre axis XX' of the user's head 3. The rings 2 are connected to each other by flexible connecting elements 4, for example made of the same material as the rings, in this example silicone. The connecting elements 4 are precisely positioned on the support 20a to allow both the support 20a to adapt to the shape of the user's head 3, and to allow the support to be held on the head 3, as described in detail below.

The rings 2 are distributed as follows: the support 20a provides ten peripheral rings 2a, four second peripheral rings 2b and four central rings 2c. It is understood that this precise number and precise arrangement of the rings is given as an example without limitation. The number and the position of the rings 2 can vary while remaining within the scope of the invention.

Figure 5:
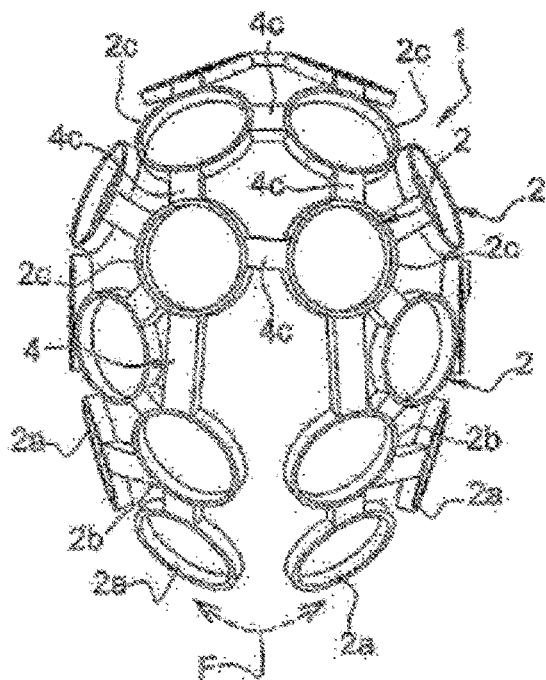
FIG. 5 is a schematic top view of the module support of the top portion of the device of the invention intended to be positioned on the user's head.
Figure 6:
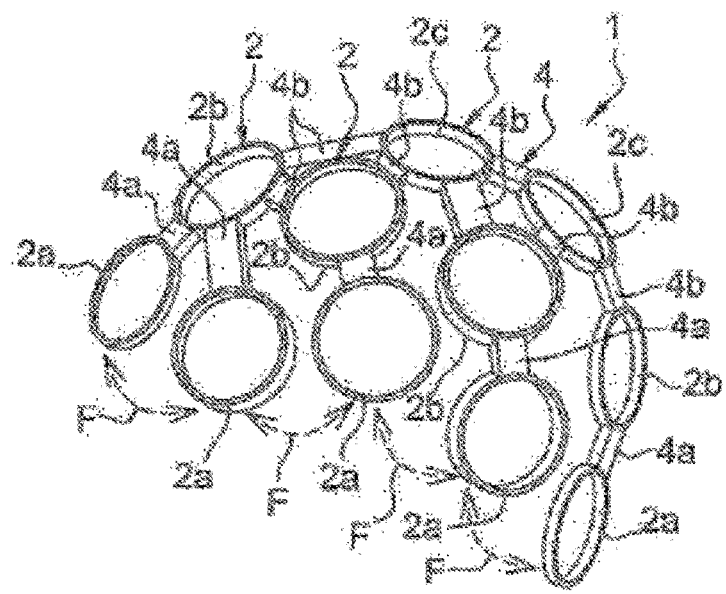
FIG. 6 is a schematic side view of the module support of the top portion of the device of the invention intended to be positioned on the user's head.
Figure 7:
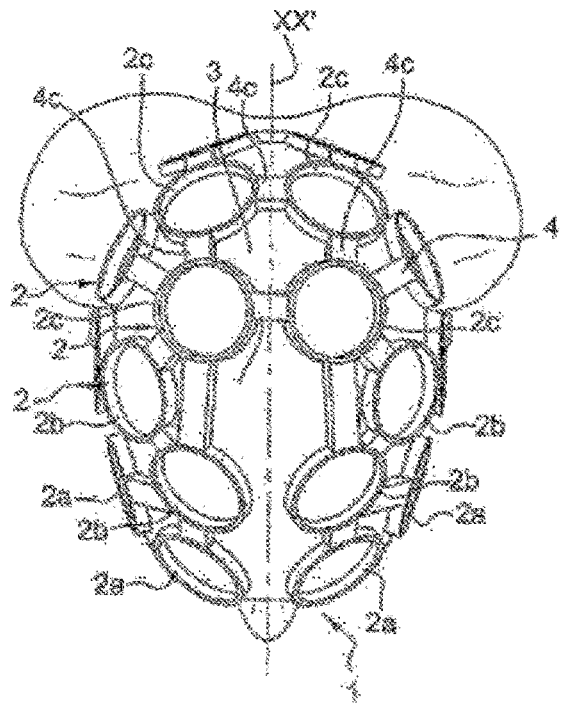
FIG. 7 is a schematic top view of the module support of the top portion of the device of the invention in position on the user's head.

FIG. 5, in which the rings 2a, 2b, 2c have been numbered 2a1, 2a2, 2a3, 2a4, 2a5, 2b1, 2b2, 2b3, 2b4, 2c1 and 2c2, is used to describe their functionality, it being understood that this FIG. 5 represents only half of the support 20a. The four peripheral rings 2a1, 2a2 and the two second peripheral rings 2b1 located towards the front of the head 3 are designed to reach the frontal lobe. The six peripheral rings 2a2, 2a3 and 2a4 extending from the second front peripheral ring are intended to reach the temporal lobe. The four central rings 2c1, 2c2 and the four second peripheral rings 2b2, 2b3 located above the patient's ears are intended to reach the parietal lobe. The four most rearward peripheral rings 2a4, 2a5 are intended to reach the cerebellum. And the two second peripheral rings 2b4 located above the rearmost peripheral ring, and the two peripheral rings 2a4 at the front of the rearmost peripheral rings 2a5, are intended to reach the occipital lobe. All the rings 2 also allow the thalamus, hippocampus and tonsils to be reached more deeply.

The four central rings 2c are connected to each other by central junctions 4a. The second peripheral rings 2b are connected to the central rings 2c by the second peripheral junctions 4b. Some second peripheral rings 2b are also connected to each other by the second peripheral junctions 4b. The peripheral rings 2a are each connected to a second peripheral ring 2b by a peripheral junction 4a. On the other hand, the peripheral rings 2a are not connected to each other by junctions. It is possible to provide that one of the junctions 4a, 4b, 4c includes a flat area where a patient identification label can be attached.

The absence of a connection between the peripheral rings 2a allows the support 20a to adapt to the shape of the patient's head by opening to a greater or lesser extent. Remaining within the scope of the invention, some peripheral rings 2a could be linked together while providing this adaptation functionality. On the other hand, if all the peripheral rings 2a are connected to each other, the support 20a will not be able to adapt to different head shapes.

For the second peripheral rings 2b, some are connected to each other so that the support is sufficiently strong to remain in place on the head and hold the modules in place in the rings. The fact that some second peripheral rings 2b are not connected to each other also allows the functionality of adapting the support 20a to any head shape to be maintained.

The presence or absence and the position of the second peripheral junctions 4b and the peripheral junctions 4a are assessed by the skilled person in a compromise between the rigidity of the support 20a necessary to allow it to be maintained in position on the patient's head and to hold the module(s), and the adaptation character of the support 1 to any head shape. The presence or absence of these junctions may vary according to the number of rings 2 present on the support 1 or the rigidity of the materials used to make the rings 2 and the junctions 4.

In any case, it is essential that at least some of the peripheral rings 2a are not connected to each other, and preferably not all the peripheral rings 2a are connected to each other. It also seems important for the rigidity of the support that, on the contrary, the central rings 2c are connected to each other by junctions 4a. The full connection of the central rings 2c depends on the number of central rings 2c used.

By way of example, the module support 20 can be made in one piece by silicone moulding.

Figure 8:
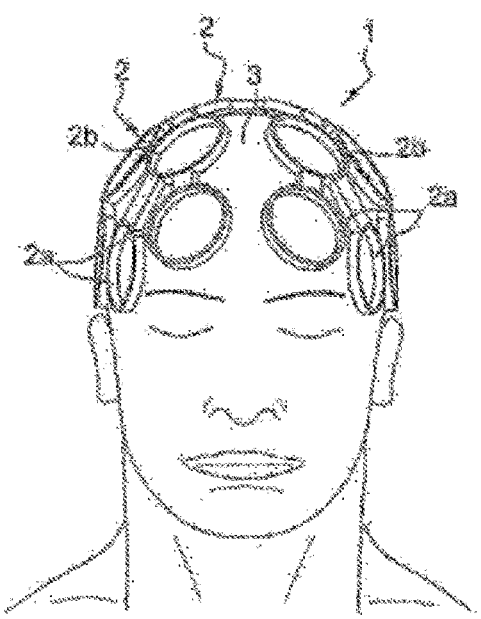
FIG. 8 is a schematic front view of the module support of the top portion of the device of the invention in position on the user's head.
Figure 9:
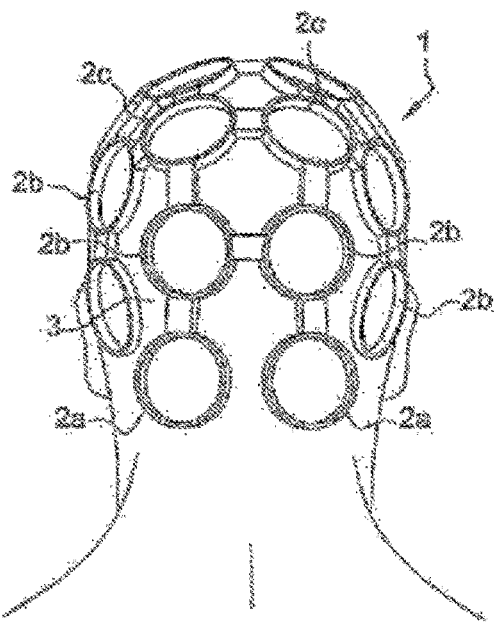
FIG. 9 is a schematic back view of the module support of the top portion of the device of the invention in position on the user's head.
Figure 10:
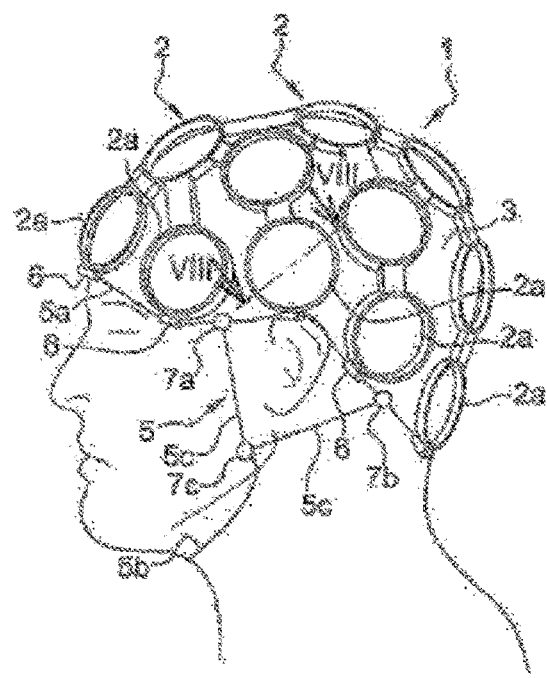
FIG. 10 is a schematic side view of the module support of the top portion of the device of the invention in position on the user's head.

With reference to FIG. 8, to further improve the holding of the support 20a on the head and to precisely position the rings 2 towards the areas of the brain to be treated, a controlled tightening strap 5 is provided. This strap 5 includes a first connecting part 5a which connects each peripheral ring 2a through a tubular element 6 arranged at the lower peripheral edge of each peripheral ring 2a.

The strap 5 also includes a chin strap 5b connected to the first connecting part 5a by four connecting elements 5c, passing in pairs on either side of the patient's ear.

Three clamping points 7a, 7b, 7c can be provided, of which two clamping points 7a, 7b are located at the junction of the connecting elements 5c and the first connecting part 5a, and the third clamping point is located at the junction between the chin strap 5b and the two connecting elements 5c.

As described above in reference to FIG. 3, to further improve the performance of transcutaneous irradiation modules 10 in the rings 2, a groove 8 can be provided on the inner side of the ring 2. This groove 8 is intended to coincide with the circular rib 11 on the outer surface of the associated module 10. The presence of the groove 8 not only improves the grip of the module, but also provides a more precise positioning of the module so that radiation is precisely directed towards the targeted areas of the brain or abdomen.

With reference to FIG. 2, the module support 20b for the bottom portion 9 of the invention also includes rings 2 connected together by junctions 4, the rings 2 and the junctions 4 being identical to those described above for the module support 20a. The module support 20d includes for this purpose peripheral rings 2a and central rings 2c ensuring the distribution of the rings 2 along four lines extending vertically between the groin and the stomach and horizontally over the width of the abdomen 16. As with the module support 20a, the peripheral rings 2a are not connected to each other by junctions 4 to best adapt to the abdominal morphology of the user.

For holding the bottom portion of the invention in position on the abdomen 16 of the bottom portion 9 of the device, it is possible to provide loops 19 each attached to the opposite ends of the same line of rings 2 and in which a belt strap can be inserted for fixing.

System

The present invention also relates to a system comprising the device according to the present invention, comprising a control console comprising a control interface for configuring the parameters of each of the at least one irradiation source 14a, 14b, 14c and a communication interface for providing digital control instructions to said device.

Treatment

The present invention also relates to the device or system according to the present invention, configured for the prevention and/or treatment of neurological disorders and/or neurodegenerative diseases in a user in need thereof. In particular, the device or system according to the present invention is configured for the prevention and/or treatment of Alzheimer's disease, Parkinson's disease and/or Huntington's disease.

The present invention also relates to a method of treating neurological disorders and/or neurodegenerative diseases, preferably Alzheimer's disease, Parkinson's disease and/or Huntington's disease, including transcutaneous irradiation of a user in need thereof by means of the device or system according to the present invention.

In an embodiment, the user is/was diagnosed with a neurological disorder and/or neurodegenerative disease, preferably Alzheimer's disease, Parkinson's disease and/or Huntington's disease. The user may be diagnosed by medical personnel (such as a doctor or nurse), a family member or acquaintance, who recognise, appreciate, determine, confirm, conclude, think or decide that the user is affected with a neurological disorder and/or neurodegenerative disease, preferably Alzheimer's disease, Parkinson's disease and/or Huntington's disease.

In an embodiment, the user is a man or a woman, over 20 years old, over 30 years old, over 40 years old, over 50 years old, over 60 years old, over 70 years old or over 80 years old.

In an embodiment, the transcutaneous irradiation treatment may be performed by the device or system of the invention simultaneously on the head or abdomen, or consecutively. In an embodiment, the transcutaneous irradiation time per session is between 5 and 60 minutes, preferably between 5 and 40 minutes, preferably between 10 and 30 minutes, preferably about 25 minutes. In an embodiment, the transcutaneous irradiation treatment is performed once a day, twice a day or three times a day, preferably once a day. In an embodiment, the transcutaneous irradiation treatment is performed 1 to 7 times a week, for example 1 day a week, 2 days a week, 3 days a week, 4 days a week, 5 days a week, 6 days a week or 7 days a week. In an embodiment, the total duration of the transcutaneous irradiation treatment is between 1 and 365 days, depending on the frequency of the treatments, the pathology treated and the general condition of the patient.

In a preferential embodiment, the transcutaneous irradiation treatment is performed for a total duration of 2 months, at the rate of one 25-minute session per day for five days every seven days.

EXAMPLES

Example 1

Tests were carried out to evaluate the efficacy of the device of the invention. More specifically, the efficacy of the device of the invention on reducing the pathology induced by the injection of beta-amyloid in mice was evaluated. These tests also made it possible to determine the irradiation protocol used to treat neurodegenerative diseases such as Alzheimer's disease.

The animal model used to test the device of the invention is the non-transgenic $A\beta_{25-35}$ model of Alzheimer's disease consisting of intracerebral-ventricular injection in mice of amyloid peptide $A\beta_{25-35}$ in oligomeric form. The presence of amyloid peptides has been identified in the brains of Alzheimer's patients; peptide $A\beta_{25-35}$ proves to be one of the most neurotoxic. It has been shown that intracerebral-ventricular injection of the peptide $A\beta_{25-35}$ results, seven days later in the brain, in the presence of neuroinflammation and reactive gliosis, activation of pro-apoptotic caspases, oxidative stress, reduction in the number of pyramidal cells in the hippocampus, loss of cholinergic neurons and serious memory problems. Very interestingly, the injection of the $A\beta_{25-35}$ peptide results in the development of a pathology that has all the characteristics of Alzheimer's disease in humans, with in particular the accumulation of endogenous A species but also a hyperphosphorylation of the tau protein, as observed in the physiopathology of Alzheimer's disease.

On day 1, a group of "test" mice were injected with amyloid peptide $A\beta_{25-35}$ at a dose of 9 nmol/mouse to induce amyloid toxicity; and another group of "negative control" mice was injected with peptide Sc.Aβ (scrambled amyloid-R protein 25-35) at a dose of 9 nmol/mouse.

Part of the "test" group of mice was subjected to transcutaneous irradiation treatment from day 1 (2 hours after injection of amyloid peptide $A\beta_{25-35}$) on day 10. The irradiation treatment was performed either on the head alone, or on the abdomen alone, or on the head and abdomen. The irradiation devices used are either according to the invention or outside the scope of the invention (in particular for devices applied only to the head, or only to the abdomen). Treatments are performed once or twice a day. The different devices used and compared will be explained below.

On days 8 to 10, behavioural tests are performed on all groups of mice (Sc.Aβ without treatment, $A\beta_{25-35}$ without treatment, $A\beta_{25-35}$ with treatment).

The first behavioural test conducted on day 8 assesses the alteration of spontaneous spatial memory in mice using a test to assess alternation performance in a Y-shaped maze. The maze therefore has three arms. Each mouse is positioned at the end of an arm and can move freely in the maze during an 8-minute session. The movement of each mouse, including returns in the same arm, is visually checked. An alternation is defined as entries in all three arms on several consecutive occasions. The maximum number of alternations is the total number of entries in the arms minus two.

The percentage of alternation is calculated as: (the number of actual alternations/the number of maximum alternations)×100. The results of this first behavioural test are presented in FIGS. 11, 17 and 23.

The second behavioural test on days 9 and 10 assesses long-term contextual memory, otherwise known as the "passive avoidance test". This test is performed on day 10 in two steps with a training session on day 9. The device under test is a two-compartment box, one of which is illuminated and the other immersed in darkness, with a grid floor. A guillotine-type closing door separates the two compartments. Shocks can be generated on the grid board of the dark compartment. Initially, the door separating the two compartments is closed. For the training session, each mouse is placed in the illuminated compartment. After 5 seconds, the door is open. When the mouse enters the dark compartment, electric shocks are generated on the grid. On day 10, the mouse is again placed in the illuminated compartment with the door closed. The door is open and two parameters are measured: the latency time, i.e. the time after which the mouse enters the dark compartment, and the escape time, i.e. the time after which the mouse leaves the dark compartment. The results of these two subtests (latency time and escape time) are shown in FIGS. 12, 18 and 24 and FIGS. 13, 19 and 25.

On day 10, the mice are euthanised. The hippocampus and frontal cortex of the mice are dissected. Levels of lipid peroxidation in the hippocampus are determined in CHP equivalents per milligram of tissue and as a percentage of the control group (untreated Sc.Aβ). The results are shown in FIGS. 14, 20 and 26. The level of glial fibrillary acidic protein (GFAP) is also determined in the hippocampus by ELISA. The results are expressed as a percentage of the control group (Sc.Aβ without treatment) and presented in FIGS. 15, 21 and 27. In the hippocampus, the level of tumour necrosis factor (TNFα) is also determined by ELISA. The results are expressed as a percentage of the control group (Sc.Aβ without treatment) and presented in FIGS. 16, 22 and 28.

Levels of interleukin-1 beta (IL-1β) (FIG. 23) and interleukin-6 (IL-6) (FIG. 24) are also determined in the frontal cortex. These two cytokines reflect the inflammatory state of brain tissue. The levels of the Bax and Bcl2 proteins in the cerebral cortex, whose ratio reflects apoptosis (FIG. 25), of tau protein (pTau) Thr81 (FIG. 26) and of amyloid protein-β (1-42) ($A\beta_{1-42}$) (FIG. 27) are also determined. Abnormally produced amyloid protein-β (1-42) and abnormally phosphorylated tau protein are characteristic of Alzheimer's disease.

Finally, histological analyses are performed on histological sections of the C1 region of the hippocampus. A visual count is performed to determine the average number of activated astrocytes for series of sections using glial fibrillary acidic protein (GFAP) as a marker. A visual count is also performed to determine the average number of activated microglial cells using the Iba1 protein as a marker. The activation of astrocytes and of microglial cells accounts for the neuroinflammatory processes involved in neurological pathologies.

It should be noted that for the results presented in FIGS. 11 to 35, the results obtained by injecting Sc.Aβ without treatment constitute a first reference control since this injection did not modify the behaviour of the mice or the rate of markers tested. The results obtained by injecting $A\beta_{25-35}$ without treatment constitute a second reference control.

It should also be noted that the indications ###, ## and # mean respectively a total, excellent and good adequacy with the control group (Sc.Aβ without treatment) and the indications \*\*\*,\*\* and \* mean respectively a total, consequent and sensitive absence inadequate with the control (Sc.Aβ without treatment).

Referring to FIGS. 11 to 16, these figures illustrate the results obtained by the tests mentioned above for irradiation treatments performed once a day under the following operating conditions:

Reference 30: injection of Sc.Aβ without treatment (control 1).

Reference 31: injection of $A\beta_{25-35}$ without treatment (control 2).

Reference 32: Injection of $A\beta_{25-35}$ with 10-minute treatment once a day simultaneously on the head and on the abdomen by "device A".

Reference 33: Injection of $A\beta_{25-35}$ with 20-minute treatment once a day simultaneously on the head and on the abdomen by "device A".

Reference 34: Injection of $A\beta_{25-35}$ with 5-minute treatment once a day simultaneously on the head and on the abdomen by "device B".

Reference 35: Injection of $A\beta_{25-35}$ with 2.5-minute treatment once a day simultaneously on the head and on the abdomen by "device C".

Reference 36: Injection of $A\beta_{25-35}$ with 10-minute treatment once a day simultaneously on the head and on the abdomen by "device D".

Reference 37: Injection of $A\beta_{25-35}$ with 10-minute treatment once a day simultaneously on the head and on the abdomen by "device E".

Reference 38: Injection of $A\beta_{25-35}$ with 10-minute treatment once a day simultaneously on the head and on the abdomen by the "device F".

"Device A", comprising a top portion 1 and a bottom portion 9, each comprising a transcutaneous irradiation module 10 consisting of:
  a light-emitting diode (LED) generating a beam emitting in the infrared spectrum at a wavelength of 850 nanometres;
  a light-emitting diode (LED) generating a beam emitting in the red spectrum at a wavelength of 625 nanometres;
  a pulsed laser diode generating a beam emitting in the infrared spectrum at a wavelength of 850 nanometres, having a pulse duration of between 120 and 150 nanoseconds, a pulse train repetition frequency of 10 kHz (or 0.1 milliseconds), and a pulse power of between 1 watt and 7 watts;
  A voltage of 2.30 V;
  a static and circular magnetic field of 200 militeslas.

The treatment is established in pulsed mode at an overall modulation frequency of 10 hertz for the head and 1000 hertz for the abdomen.

"Device B", comprising a top portion 1 and a bottom portion 9, each comprising a transcutaneous irradiation module 10 consisting of:
  a light-emitting diode (LED) generating a beam emitting in the infrared spectrum at a wavelength of 850 nanometres;
  a light-emitting diode (LED) generating a beam emitting in the red spectrum at a wavelength of 625 nanometres;
  a pulsed laser diode generating a beam emitting in the infrared spectrum at a wavelength of 850 nanometres, having a pulse duration of between 120 and 150 nanoseconds, a pulse train repetition frequency of 10 kHz (or 0.1 milliseconds) and a pulse power of between 1 watt and 7 watts;
  a static and circular magnetic field of 200 militeslas.

The treatment is established in continuous mode, i.e. without overall modulation frequency (0 hertz) for the head and for the abdomen.

"Device C", comprising a top portion 1 and a bottom portion 9, each comprising a transcutaneous irradiation module 10 consisting of:
- a light-emitting diode (LED) generating a beam emitting in the red spectrum at a wavelength of 625 nanometres;
- a continuous type laser diode generating a beam emitting in the infrared spectrum at a wavelength of 850 nanometres; and
- a static and circular magnetic field of 200 milliteslas.

The treatment is established in pulsed mode at an overall modulation frequency of 10 hertz for the head and 1000 hertz for the abdomen.

"Device D", comprising a top portion 1 and a bottom portion 9, each comprising a transcutaneous irradiation module 10 consisting of:
- a light-emitting diode (LED) generating a beam emitting in the infrared spectrum at a wavelength of 850 nanometres;
- a light-emitting diode (LED) generating a beam emitting in the red spectrum at a wavelength of 625 nanometres;
- a pulsed laser diode generating a beam emitting in the infrared spectrum at a wavelength of 850 nanometres, having a pulse duration of between 120 and 150 nanoseconds, a pulse train repetition frequency of 10 kHz (or 0.1 milliseconds) and a pulse power of between 10 watts and 13 watts; and
- a static and circular magnetic field of 200 milliteslas.

The treatment is established in pulsed mode at an overall modulation frequency of 10 hertz for the head and 1000 hertz for the abdomen.

"Device E", comprising a top portion 1 and a bottom portion 9, each comprising a transcutaneous irradiation module 10 consisting of:
- three light-emitting diodes (LEDs) generating a beam emitting in the infrared spectrum at a wavelength of 850 nanometres; and
- a static and circular magnetic field of 200 milliteslas.

The treatment is established in pulsed mode at an overall modulation frequency of 10 hertz for the head and 1000 hertz for the abdomen.

"Device F", comprising a top portion 1 and a bottom portion 9, each comprising a transcutaneous irradiation module 10 consisting of:
- a light-emitting diode (LED) generating a beam emitting in the infrared spectrum at a wavelength of 850 nanometres;
- a light-emitting diode (LED) generating a beam emitting in the red spectrum at a wavelength of 625 nanometres;
- a pulsed laser diode generating a beam emitting in the infrared spectrum at a wavelength of 850 nanometres, having a pulse duration of between 80 and 100 nanoseconds, a pulse train repetition frequency of 10 kHz (or 0.1 milliseconds) and a pulse power of between 1 watt and 7 watts;
- without a magnetic field.

The treatment is established in pulsed mode at an overall modulation frequency of 10 hertz for the head and 1000 hertz for the abdomen.

It can be seen that the most effective treatment on the results presented in FIGS. 11 to 16 is the treatment provided by "device A" for 10 minutes of treatment. At 20 minutes of treatment with "device A", the results are also very significant except for the GFAP level and the TNFα level. The treatment performed by "device F" (without magnetic field) shows excellent results for the first behavioural test (FIG. 11) and on GFAP and TNFα levels but less satisfactory results for the second behavioural test and on lipid peroxidation levels. The treatment provided by "device D" has good or even excellent results for the second behavioural test (FIGS. 12 and 13) as well as on the level of lipid peroxidation and on the TNFα level. Devices "A", "B", "D" and "F" thus present at least in part significant results illustrating, compared with the second control 31, a substantial attenuation of both behavioural and marker pathologies induced by the $A\beta_{25\text{-}35}$ peptide. On the other hand, the treatments provided by "devices C" and "E" do not show a significant effect. The need to operate with a pulsed laser in the device of the invention is observed. This important feature is surprising in two respects. First, all the devices shown in FIGS. 11 to 16 are in pulsed mode (10 hertz for the head and 1000 hertz for the abdomen). The need to operate with a laser of the same pulsed type is therefore surprising since it results in a double pulse (the pulse frequencies will be more precisely mentioned in reference to FIGS. 17 to 22). In addition, it could be expected that the higher the pulse power, the greater the effect, which is not the case since with a laser with pulse power between 10 and 13 watts ("device D"), the results are less satisfactory than for a pulse power between 1 and 7 watts (device "A" and "F" in particular).

Now referring to FIGS. 17 to 22, these figures illustrate the results obtained by the tests mentioned above for irradiation treatments performed once or twice a day under the following operating conditions:

Reference 30: injection of Sc.Aβ without treatment (control 1).

Reference 31: injection of $A\beta_{25\text{-}35}$ without treatment (control 2).

Reference 39: Injection of $A\beta_{25\text{-}35}$ with 2.5-minute treatment twice daily only on the head with the "device A" described above.

Reference 40: with 2.5-minute treatment twice daily simultaneously on the head and on the abdomen with the "device A" described above.

Reference 41: with 5-minute treatment twice a day simultaneously on the head and on the abdomen with the "device A" described above.

Reference 42: with 10-minute treatment once a day simultaneously on the head and on the abdomen with the "device A" described above (equivalent to reference 32 in FIGS. 11 to 16).

It can be seen that the most effective treatment on the results presented in FIGS. 17 to 22 corresponds to reference 42, i.e. the treatment provided by device A for 10 minutes of treatment once a day simultaneously on the head and on the abdomen. Reference 41, which is the same treatment time but spread over two sessions per day, is also highly effective but significantly less effective than reference 42. On the other hand, the results corresponding to references 39 and 40 are insufficient (although it should be noted that good results were obtained for reference 40 on the TNFα level), which shows, on the one hand, the need, for the attenuation of this type of pathology, of a device suitable for being positioned on the head and on the abdomen to carry out an irradiation treatment on these two zones, and on the other hand a minimum irradiation time that can be evaluated at around 2.5 minutes.

Now referring to FIGS. 23 to 28, these figures illustrate the results obtained by the tests mentioned above for irradiation treatments performed once a day under the following operating conditions:

Reference 30: injection of Sc.Aβ without treatment (control 1).

Reference 31: injection of Aβ$_{25-35}$ without treatment (control 2).

Reference 43: injection of Aβ$_{25-35}$ with 10-minute treatment once a day simultaneously on the head and on the abdomen with the "device A" described above (equivalent to reference 32 in FIGS. 11 to 16 and reference 42 in FIGS. 17 to 22).

Reference 44: injection with 20-minute treatment once a day only on the head with the "device A" described above.

Reference 45: injection with 20-minute treatment once a day only on the abdomen with the "device A" described above.

Reference 46: injection of Aβ$_{25-35}$ with 10-minute treatment once a day simultaneously on the head and on the abdomen with the "device A" described above. The treatment is established in pulsed mode at 1000 hertz for the head and for the abdomen.

Reference 47: injection of Aβ$_{25-35}$ with 10-minute treatment once a day simultaneously on the head and on the abdomen with the "device A" described above. The treatment is established in pulsed mode at 10 hertz for the head and for the abdomen.

Reference 48: injection of Aβ$_{25-35}$ with 10-minute treatment once a day simultaneously on the head and on the abdomen with the "device B" described above. Treatment is established in continuous mode (at 0 hertz) for the head and for the abdomen.

It can be seen that the treatments corresponding to references 43, 46 and 47 are the most effective, showing that treatments established in pulsed mode at frequencies between 10 and 1000 hertz are the most effective. The treatment corresponding to reference 48 at 0 hertz is also effective due to the presence of the pulsed laser used. The results corresponding to references 44 and 45 confirm the essential feature of the present invention according to which the device of the invention must include a portion positioned on the head and a portion positioned on the abdomen to perform an irradiation treatment on these two zones.

Now referring to FIGS. 29 to 33, these figures illustrate the results obtained by the tests mentioned above for irradiation treatments performed once a day under the following operating conditions:

Reference 30: injection of Sc.Aβ without treatment (control 1).

Reference 31: injection of Aβ$_{25-35}$ without treatment (control 2).

Reference 49: with 10-minute treatment once a day simultaneously on the head and on the abdomen with the "device A" described above. The treatment is established in pulsed mode at 10 hertz for the head and for the abdomen.

Reference 50: with 10-minute treatment once a day simultaneously on the head and on the abdomen with the "device F" (without magnetic field) described above. The treatment is established in pulsed mode at 10 hertz for the head and 1000 hertz for the abdomen.

As with the results corresponding to references 32 and 38 in FIGS. 11 to 16, it can be seen that the presence of the magnetic field allows better results to be obtained, particularly on markers of cerebral inflammation (FIGS. 29 and 30).

Finally, referring to FIGS. 34 and 35, these figures illustrate the results obtained by the tests mentioned above for irradiation treatments performed once a day under the following operating conditions:

Reference 30: injection of Sc.Aβ without treatment (control 1).

Reference 31: injection of Aβ$_{25-35}$ without treatment (control 2).

Reference 51: with 10-minute treatment once a day simultaneously on the head and on the abdomen with the "device A" described above. The treatment is established in pulsed mode at 10 hertz for the head and for the abdomen.

It can be seen that the injection of Aβ$_{25-35}$ resulted in the activation of astrocytes (visually detectable by an extension of their branches compared with resting astrocytes) as well as the activation of microglial cells (visually detectable by a typical amoeboid morphology). The treatment with the "device A" of the invention significantly reduced the number of activated astrocytes and microglial cells.

Example 2

Materials and Methods

Materials

Animals

Ninety-six SWISS mice, 5 weeks old and weighing between 30 and 35 g, obtained from JANUARY (Saint Berthevin, France), were used for this study. The mice were raised in groups with access to water and food ad libitum (#04C, Safe Diet, Augy France) with the exception of behavioural test periods. The animal housing facility was maintained at a constant temperature and humidity, over a day/night cycle of 12 h/12 h. Mice were identified by means of markings on the tail with a permanent marker.

The health, appearance, activity and weight of the mice were monitored daily during the study.

Treatment Device Used

The transcutaneous irradiation device "RGn530" used comprises a top portion 1 and a bottom portion 9, each portion comprising a transcutaneous irradiation module 10. Each transcutaneous irradiation module 10 includes:

1 laser diode 14a generating a beam emitting in the infrared spectrum, at a wavelength of 850 nanometres, intrinsic pulse train of 15 kHz, pulse duration of 90 to 110 nanoseconds, peak pulse power of 1 to 11 watts, supply voltage of 4.24 volts;

1 light-emitting diode 14b generating a beam emitting in the red spectrum, at a wavelength of 640 nanometres;

1 light-emitting diode 14c generating a beam emitting in the infrared spectrum, at a wavelength of 850 nanometres; and a static and circular magnetic field of 200 milliteslas.

The treatment is established in pulsed mode at 10 hertz for the head and for the abdomen.

The pulse power of the laser diode $P_{max}$ as mentioned in this example is between 11 and 13 watts (corresponding to a duration between 130 and 150 nanoseconds).

The pulse power of the laser diode $P_{min}$ as mentioned in this example is between 3 and 5 watts (corresponding to a duration of between 40 and 60 nanoseconds).

Methods

Preparation and Injection of β-Amyloid Peptides

The mice were first anaesthetised for 5 minutes with 2.5% isoflurane.

After restraint, the injections were made into the lateral cerebral ventricle using a stainless-steel syringe with a diameter of 28 mm and a length of 4 mm. A volume of 3 μL was gradually injected over a period of 30 seconds, the needle was then removed 30 seconds after injection (Haley et al., 1957. *Br J Pharmacol Chemother.* 12(1):12-5).

Each animal received an injection of 9 nmol of the β-amyloid peptide (Aβ$_{25-35}$—CAS 131602-53-4 Genepep, France—vehicle used: sterile double-distilled water) or the "scramble" control peptide (Sc.Aβ—Genepep, France—vehicle used: sterile double-distilled water) according to the protocols described above (Maurice et al., 1996. *Brain Res.* 731(1-2):249-53; Maurice et al., 1998. *Neuroscience.* 83(2): 413-28; Meunier et al. 2006. *Br J Pharmacol.* 149(8):998-1012; Meunier et al., 2013. *Eur J Pharmacol.* 698(1-3):193-9; Villard et al., 2009. *Neuropsychopharmacology.* 34(6): 1552-66; and Villard et al., 2011. *J Psychopharmacol.* 25(8):1101-17).

Behavioural Tests

Y-Maze Test for Evaluation of Short-Term Spatial Memory

On day 8 of the study, all mice were tested in a Y-maze test to evaluate short-term spatial memory.

The Y-maze test was manufactured in grey polyvinyl chloride according to Itoh et al. (1993. *Eur J Pharmacol.* 236(3):341-5) and Hiramatsu et al. (1999. *Eur J Pharmacol.* 367(2-3):151-5). Each arm is 40 cm long, 13 cm high, 3 cm wide at the bottom and 10 cm wide at the edges. The arms converge at the same angle.

Each mouse is placed at the end of an arm and left free to move inside the maze for 8 minutes. The series of entries into one arm, including the return to the same arm, were observed. An alternation is defined as consecutive entries into each of the three arms. The maximum number of alternations is calculated by subtracting two from the total number of entries. The percentage of alternation corresponds to the number of alternations divided by the maximum number of alternations multiplied by 100. The parameters considered are the percentage of alternation, or memory index, and the total number of entries, or exploration index (Maurice et al., 1996. *Brain Res.* 731(1-2):249-53; Maurice et al., 1998. *Neuroscience.* 83(2):413-28; Meunier et al. 2006. *Br J Pharmacol.* 149(8):998-1012; Meunier et al., 2013. *Eur J Pharmacol.* 698(1-3):193-9; Villard et al., 2009. *Neuropsychopharmacology.* 34(6):1552-66; and Villard et al., 2011. *J Psychopharmacol.* 25(8):1101-17).

Animals with extreme behaviour (i.e., percentage of alternation <20% or >90%) are excluded from the data. In this study, no tested animals were excluded from the data.

Passive Avoidance Test for the Evaluation of Long-Term Contextual Memory

On days 9 and 10 of the study, all mice were tested in a step-through passive avoidance (STPA) test to assess long-term contextual memory.

The test device consists of a box (size 15×20×15 cm high) with two compartments. One compartment has white walls and the other has black walls and a mesh floor. A guillotine door separates the compartments. A 60 watt lamp positioned 40 cm above the device illuminates the white compartment. A scrambled electric shock (0.3 mA for 3 seconds) is sent through a scrambled electric shock generator (Lafayette instruments, Lafayette, United States).

The guillotine door is kept closed during the training phase. The animal is placed in the white compartment during this phase. After 5 seconds, the door is open. When the mouse enters the black compartment and has placed its legs on the screen, an electric shock is sent to the screen floor for 3 seconds. Step-Through Latency (STL) and the number of vocalization are observed.

The retention test is repeated 24 hours after training. Each mouse is placed in the white compartment. After 5 seconds, the guillotine door is opened and entry and avoidance latencies are observed for up to 300 seconds (Meunier et al., 2006. *Br J Pharmacol.* 149(8):998-1012; Villard et al., 2009. *Neuropsychopharmacology.* 34(6):1552-66; and Villard et al., 2011. *J Psychopharmacol.* 25(8):1101-17).

Animals with observed latencies of less than 10 seconds during training and retention testing are excluded from the data. In this study, no tested animals were excluded from the data.

Sample Collection

On day 10 of the study protocol, the animals were killed by decapitation without euthanasia.

For 12 animals per group, blood was collected in EDTA tubes and the plasma was separated.

For 12 animals per group, the brain was quickly extracted and dissected on a metal plate cooled by ice to separate the two hippocampi, the cortex and the rest of the brain. All tissues were frozen in dry ice and stored at −80° C.

After laparotomy, the caecum was fully incised and its contents aliquoted into two Eppendorf tubes.

Measurement of Lipid Peroxidation.

Six of the twelve hippocampi collected on day 10 for each group were used to measure lipid peroxidation activity as described in Hermes-Lima et al. (1995. *Free Radic Biol Med.* 19(3):271-80).

After thawing, the samples were homogenised in cold methanol (1/10 weight/v), centrifuged at 1000 g for 5 minutes. The supernatant was then collected into an Eppendorf tube. The reaction volume for each homogenate was added to a solution comprising 1 mM FeSO$_4$, 0.25 mM H$_2$SO$_4$ and 1 mM xylenol orange and incubated for 30 minutes at room temperature.

After reading the absorbance at 580 nm (A$_{550}$1), 10 μL of cumene hydroperoxide [1 mM] (CHP) was added to the sample. The absorbance at 580 nm was then measured after 30 minutes of incubation at room temperature (A$_{580}$2). The level of lipid peroxidation is calculated in CHP equivalent according to the formula: (A$_{580}$1/A$_{580}$2×[CHP nmol]) and expressed by mass of tissue as a percentage of the level in the control group (Control peptide (Sc.Aβ)—no treatment).

Measurement of TNFα Level

The hippocampi collected on day 10 for each group were used to measure the quantity of TNFα by ELISA (product number EMTNFA, ThermoScientific, USA).

After thawing, the samples were homogenised in a buffered solution (150 mM Tris-NaCl, pH 7.5) and sonicated for 20 seconds. After centrifugation (16500 g for 15 minutes at 4° C.), the supernatant or plasma was then used for the ELISA in accordance with the manufacturer's instructions. For each test, the absorbance was measured at 450 nm and the concentration of TNFα calculated using the standard curve.

The results are expressed in pg per mg of tissue. All samples were tested in duplicate.

Statistical Analysis

All values, with the exception of avoidance latency and analysis of the composition of the intestinal microbiota, are expressed as mean±standard deviation of the mean.

The statistical analysis used for each treatment is the one-way analysis of variance (ANOVA, F-value) followed by Dunnett's multiple comparison test. The analysis of avoidance latency measures does not follow a Gaussian distribution due to the maximum threshold value used. A non-parametric Kruskal-Wallis ANOVA (H-value) was therefore used. The p<0.05 values were considered statistically significant.

Determination of the Composition of the Intestinal Microbiota

Bacterial populations in caecum samples collected on day 10 of the protocol were analysed by high-throughput sequencing (MiSeq technology, Illumina, USA) of the 16S rRNA variable region V12-V4 amplified by universal primers.

For each sample, the sequence library was used to identify the taxonomic units present. For the phyla Firmicutes, Tenericutes and Deferribacteres, a histogram representation of the results was used and the Mann-Whitney test was used for statistical analysis.

Study Protocol

Study groups corresponding to the controls and to different treatment regimes for transcutaneous irradiation by the "RGn530" device were defined (Table 1).

For each group, the control peptide or the β-amyloid peptide was injected on day 1 of the protocol. On days 1 to 9 of the protocol, the treatment as defined in Table 1 for the different groups was applied once a day.

On day 8, short-term spatial memory was evaluated in a Y-maze test. On days 9 and 10 of the protocol, long-term contextual memory was assessed in a passive avoidance test. After the test on day 10 of the protocol, the animals were sacrificed and samples were taken.

TABLE 1

| Treatment group | Sample size | |
|---|---|---|
| 1 - Control peptide (Sc.Aβ) - no treatment | 6 | 6 |
| 2 - β-Amyloid peptide (Aβ$_{25-35}$) - no treatment | 6 | 6 |
| 3 - β-Amyloid peptide (Aβ$_{25-35}$) - RGn530 head and abdomen 3 minutes | 12 | — |
| 4 - β-Amyloid peptide (Aβ$_{25-35}$) - RGn530 head and abdomen 6 minutes | 12 | — |
| 5 - β-Amyloid peptide (Aβ$_{25-35}$) - RGn530 head and abdomen 6 minutes | 12 | — |
| 6 - β-Amyloid peptide (Aβ$_{25-35}$) - RGn530X with head and abdomen lens 6 minutes (no shaving) | — | 12 |
| 7 - β-Amyloid peptide (Aβ$_{25-35}$) - RGn530Y P$_{max}$ head and abdomen 4.5 minutes (shaving) | — | 12 |
| 8 - β-Amyloid peptide (Aβ2$_{25-35}$) - RGn530Z P$_{min}$ head and abdomen 6 minutes (shaving) | — | 12 |
| Total number of mice | 48 | 48 |

Results

Effect of Treatment on Short-Term Spatial Memory (Y-Maze Test)

The injection of Aβ$_{25-35}$ leads to a significant reduction in short-term spatial memory compared with mice injected with the control peptide (Sc.Aβ).

Transcutaneous irradiation treatment with the "RGn530" device, lasting 3 minutes at the head and abdomen, does not significantly change the reduction in short-term spatial memory observed after the injection of Aβ$_{25-35}$.

Transcutaneous irradiation treatment with the "RGn530" device lasting 6 minutes (with or without shaving) and 9 minutes at the head and abdomen level significantly and completely corrects the reduction in short-term spatial memory observed after the injection of Aβ$_{25-35}$.

Transcutaneous irradiation treatment with the "RGn530" device (with P$_{max}$ and P$_{min}$) lasting 4.5 minutes at the head and abdomen significantly and partially corrects the reduction in short-term spatial memory observed after the injection of Aβ$_{25-35}$.

No reduction in mouse motor skills was observed.

Statistical analysis: One-way ANOVA

Alt % $F_{(7; 95)}$ 22.91, p>0.001

Loc % $F_{(7; 95)}$ 0.9366, p>0.05

The results are presented in FIG. 36.

Effect of Treatment on Long-Term Contextual Memory (Passive Avoidance Test)

The injection of Aβ$_{25-35}$ leads to a significant reduction in long-term contextual memory compared with mice injected with the control peptide (Sc.Aβ).

Transcutaneous irradiation treatment with the "RGn530" device lasting 3 minutes at the head and abdomen does not significantly change the reduction in long-term contextual memory observed after the injection of Aβ$_{25-35}$.

Transcutaneous irradiation treatment with the "RGn530" device lasting 6 minutes (with or without shaving) and 9 minutes at the head and abdomen level significantly and completely corrects the reduction in long-term contextual memory observed after the injection of Aβ$_{25-35}$.

Transcutaneous irradiation treatment with the "RGn530" device (with P$_{max}$ and P$_{min}$) lasting 4.5 minutes at the head and abdomen corrects in a non-significant and partial way the long-term contextual memory reduction observed after the injection of Aβ$_{25-35}$.

No differences were observed for step-through latency (STL) and escape latency (EL) profiles.

The results are presented in FIG. 37.

Statistical analysis: Non-parametric Kruskal-Wallis ANOVA

STL H=62.05, p>0.0001

EL H=57.03, p>0.05

Effect of Treatment on Oxidative Stress in the Hippocampus (Lipid Peroxidation Test The injection of Aβ$_{25-35}$ leads to a significant increase in oxidative stress level compared with mice injected with the control peptide (Sc.Aβ).

Transcutaneous irradiation treatment with the "RGn530" device lasting 3 minutes at the head and abdomen does not significantly change the increase in oxidative stress level observed after the injection of Aβ$_{25-35}$.

Transcutaneous irradiation treatment using the "RGn530" device lasting 6 minutes (with or without shaving) and 9 minutes at the head and abdomen level significantly and completely corrects the increase in oxidative stress level observed after the injection of Aβ$_{25-35}$.

Transcutaneous irradiation treatment with the "RGn530" device (with P$_{max}$) lasting 4.5 minutes at the head and abdomen significantly and completely corrects the increase in oxidative stress level observed after the injection of Aβ$_{25-35}$.

Transcutaneous irradiation treatment with the "RGn530" device (with P$_{min}$) lasting 4.5 minutes at the head and abdomen significantly and partially corrects the increase in oxidative stress level observed after the injection of Aβ$_{25-35}$.

No differences were observed for step-through latency (STL) and escape latency (EL) profiles.

The results are presented in FIG. 38.

Statistical analysis: One-way ANOVA $F_{(7; 47)}$ 8.705, p<0.001

Effect of Treatment on Inflammation in the Hippocampus (TNFα Level)

The injection of Aβ$_{25-35}$ leads to a significant increase in the level of TNFα compared with mice injected with the control peptide (Sc.Aβ).

Transcutaneous irradiation treatment with the "RGn530" device lasting 3 minutes at the head and abdomen significantly and partially corrects the increase in TNFα level observed after the injection of Aβ$_{25-35}$.

Transcutaneous irradiation treatment with the "RGn530" device lasting 6 minutes (with or without shaving) and 9 minutes at the head and abdomen level significantly and completely corrects the increase in TNFα level observed after the injection of Aβ$_{25-35}$.

Transcutaneous irradiation treatment with the "RGn530" device (with P$_{min}$ or P$_{max}$) lasting 4.5 minutes at the head and abdomen significantly and completely corrects the increase in TNFα level observed after the injection of Aβ$_{25-35}$.

The results are presented in FIG. 39.

Statistical analysis: One-way ANOVA $F_{(7; 47)}$ 220.9 p<0.0001

Effect of the Treatment on the Composition of the Intestinal Microbiota (Abundance of Firmicutes, Tenericutes and Deferribacteres)

The injection of Aβ$_{25-35}$ leads to a significant variation in the abundance of Firmicutes, Tenericutes and Deferribacteres in the cecum, compared with mice injected with the control peptide (Sc.Aβ). In particular, the abundance of Firmicutes decreases significantly after injection of Aβ$_{25-35}$, while that of Tenericutes increases significantly.

Transcutaneous irradiation treatment with the "RGn530" device lasting 6 minutes (with shaving) at the head and abdomen results in an increase in abundance in the cecum of Firmicutes observed after the injection of Aβ$_{25-35}$.

In addition, transcutaneous irradiation treatment with the "RGn530" device lasting 6 minutes (with shaving) at the head and abdomen results in a decrease in the abundance of Tenericutes and Deferribacteres, compared with mice injected with the Aβ$_{25-35}$ peptide.

The results are presented in FIG. 40.

CONCLUSION

The injection of Aβ$_{25-35}$ leads to a reduction in short-term spatial memory and long-term contextual memory. The injection of Aβ$_{25-35}$ also leads to an increase in the level of oxidative stress and the level of TNFα.

These behavioural and biochemical deficits are reduced by daily transcutaneous irradiation treatment using the "RGn530" device. Neither shaving nor power variation (i.e., P$_{min}$ vs. P$_{max}$) affects the results obtained.

Daily transcutaneous irradiation treatment using the "RGn530" device results in an increase in the abundance of Firmicutes in the cecum, thus reducing the variation observed after the injection of Aβ$_{25-35}$; while the same daily transcutaneous irradiation treatment results in a decrease in the abundance of Tenericutes and Deferribacteres, compared with the abundance observed in untreated mice injected with the Aβ$_{25-35}$ peptide.

Of particular interest, the variation in the abundance of Firmicutes, Tenericutes and Deferribacteres observed in the Alzheimer's disease model used in this study is associated with two other neurodegenerative diseases: Huntington's disease and Parkinson's disease (Tremlett et al., 2017. *Ann Neurol.* 81(3):369-382). This finding and the observations of this study on the effect of the treatment on the composition of the intestinal microbiota therefore suggest a use of the device according to the invention in the treatment of Huntington's disease and Parkinson's disease. In accordance with this analysis, antibiotic treatment, leading to a reduction in Firmicutes abundance similar to Alzheimer's disease, has been associated with a reduction in motor skills, a symptom in Parkinson's disease (Parashar et al., 2017. *Parkinsonism Relat Disord.* 38:1-7).

The invention claimed is:

1. A transcutaneous irradiation device, comprising:
   a top portion suitable for positioning on a head of a user and including at least one top transcutaneous irradiation module including at least one top irradiation source; and
   a bottom portion suitable for being positioned on an abdomen of the user and including at least one bottom transcutaneous irradiation module including at least one bottom irradiation source,
   wherein the at least one top irradiation source of the at least one top transcutaneous irradiation module comprises at least one top pulsed laser source and the at least one bottom irradiation source of the at least one bottom transcutaneous irradiation module comprises at least one bottom pulsed laser source,
   wherein application of an overall modulation frequency to the at least one top irradiation source and to the at least one bottom irradiation source subjects the at least one top pulsed laser source and the at least one bottom pulsed laser source to a double pulse, and
   wherein the double pulse to which is respectively subjected the at least one top pulsed laser source and the at least one bottom pulsed laser source comprises:
   a first pulse, said first pulse corresponding to pulses generated by the at least one top pulsed laser source and the at least one bottom pulsed laser source, said first pulse having a pulse train comprising a repetition frequency between 1 and 25 kHz; and
   a second pulse resulting from the application of the overall modulation frequency to the pulses generated by the at least one pulsed laser source, said second pulse comprising a repetition frequency between 0 and 4000 Hz.

2. The device according to claim 1, wherein the at least one top pulsed laser source and the at least one bottom pulsed laser source generate a beam emitting in the infrared spectrum, said beam having a wavelength between 700 and 1200 nanometres and the pulse train comprising:
   a pulse duration between 20 and 200 nanoseconds,
   an impulse power of between 0.5 and 12 watts inclusive; and
   a voltage between 2 and 5 volts inclusive.

3. The device according to claim 2, wherein a repetition frequency of the beam generated by the at least one top pulsed laser source and the at least one bottom pulsed laser source is between 10 and 15 kHz inclusive.

4. The device according to claim 1, wherein the at least one top transcutaneous irradiation module and the at least one bottom transcutaneous irradiation module each comprise at least:
   the at least one pulsed laser source, said at least one pulsed laser source generating a beam emitting in an infrared spectrum;
   a light-emitting diode or an additional laser source generating a beam emitting in a red spectrum; and
   a light-emitting diode generating a beam emitting in the infrared spectrum.

5. The device according to claim 1, wherein the at least one top transcutaneous irradiation module and the at least one bottom transcutaneous irradiation module each further comprise a magnet or an electromagnet generating a static magnetic field.

6. The device according to claim 5, wherein the magnet or an electromagnet generating a static magnetic field comprises a ring shape to be arranged perpendicular to a plane of which a transcutaneous irradiation is generated by the at least one top irradiation source and the at least one bottom irradiation source.

7. The device according to claim 1, further comprising a module for synchronizing emissions of the at least one top transcutaneous irradiation module of the top portion with emissions of the at least one bottom transcutaneous irradiation module of the bottom portion, wherein beams emitted by the irradiation modules are transmitted at the overall modulation frequency, said overall modulation frequency being of about 9 to 11 Hz for each of the at least one top transcutaneous irradiation module of the top portion and the at least one bottom transcutaneous irradiation module of the bottom portion.

8. The device according to claim 1, wherein at least two top transcutaneous irradiation modules are configured to be in contact with the head of the user and at least two bottom transcutaneous irradiation modules are configured to be in contact with the abdomen of the user.

9. The device according to claim 1, wherein at least one of the at least one top transcutaneous irradiation module and the at least one bottom transcutaneous irradiation module presents a generally cylindrical shape and is held within a ring of a substantially cylindrical shape so as to ensure to be held coaxially in a cylinder axis of the ring, said ring being configured to be in contact with the user so that a beam of said at least one top irradiation source or said at least one bottom irradiation source is emitted parallel to the cylinder axis of the ring.

10. A system comprising the device according to claim 1, further comprising a control console including a control interface for configuring parameters of each of the at least one top irradiation source or bottom irradiation source and a communication interface for providing digital control instructions to said device.

11. The device according to claim 1, configured for prevention or treatment of neurological disorders and/or neurodegenerative diseases.

12. The device according to claim 11, configured for prevention or treatment of Alzheimer's disease, Parkinson's disease and/or Huntington's disease.

13. The device according to claim 1, wherein the overall modulation frequency is between 0 and 1000 Hz.

14. The device according to claim 1, wherein the overall modulation frequency between 1 and 100 Hz.

15. The device according to claim 1, wherein the overall modulation frequency around 10 Hz.

16. The device according to claim 1, wherein the overall modulation frequency applied to the at least one top pulsed laser source of the top portion of the device is different from the overall modulation frequency applied to the at least one bottom pulsed laser source of the bottom portion of the device.

17. The device according to claim 1, wherein the repetition frequency of the pulse train of the first pulse is between 10 and 15 kHz, and wherein the repetition frequency of the second pulse is between 1 and 100 Hz.

18. A transcutaneous irradiation device, comprising:
a top portion suitable for positioning on a head of a user and including at least one top transcutaneous irradiation module including at least one top irradiation source; and
a bottom portion suitable for being positioned on an abdomen of the user and including at least one bottom transcutaneous irradiation module including at least one bottom irradiation source,
wherein the at least one top irradiation source of the at least one top transcutaneous irradiation module comprises at least one top pulsed laser source and the at least one bottom irradiation source of the at least one bottom transcutaneous irradiation module comprises at least one bottom pulsed laser source,
wherein application of an overall modulation frequency to each of the at least one top pulsed laser source and the at least one bottom pulsed laser source subjects the at least one top pulsed laser source and the at least one bottom pulsed laser source to a double pulse, and
wherein at least one of the at least one top transcutaneous irradiation module and the at least one bottom transcutaneous irradiation module presents a generally cylindrical shape and is held within a ring of a substantially cylindrical shape so as to ensure to be held coaxially in a cylinder axis of the ring, said ring being configured to be in contact with a patient so that a beam of said at least one top irradiation source or said at least one bottom irradiation source is emitted parallel to the cylinder axis of the ring.

19. The device according to claim 18, configured for prevention or treatment of neurological disorders and/or neurodegenerative diseases.

20. The device according to claim 19, configured for prevention or treatment of Alzheimer's disease, Parkinson's disease and/or Huntington's disease.

\* \* \* \* \*